(12) United States Patent
Olsen et al.

(10) Patent No.: US 9,359,457 B2
(45) Date of Patent: Jun. 7, 2016

(54) PROTEIN-BASED CONJUGATES AND SELF-ASSEMBLED NANOSTRUCTURES

(75) Inventors: Bradley D. Olsen, Arlington, MA (US); Carla S. Thomas, Verona, WI (US)

(73) Assignee: Massachusetts Institute of Technology, Cambridge, MA (US)

( * ) Notice: Subject to any disclaimer, the term of this patent is extended or adjusted under 35 U.S.C. 154(b) by 361 days.

(21) Appl. No.: 13/882,035

(22) PCT Filed: Oct. 26, 2011

(86) PCT No.: PCT/US2011/057941
§ 371 (c)(1),
(2), (4) Date: Jul. 11, 2013

(87) PCT Pub. No.: WO2012/058343
PCT Pub. Date: May 3, 2012

(65) Prior Publication Data
US 2013/0280782 A1  Oct. 24, 2013

Related U.S. Application Data

(60) Provisional application No. 61/406,623, filed on Oct. 26, 2010.

(51) Int. Cl.
*C08F 20/56* (2006.01)
*A61K 47/48* (2006.01)
*B82Y 5/00* (2011.01)
*C12N 9/96* (2006.01)

(52) U.S. Cl.
CPC ........... *C08F 20/56* (2013.01); *A61K 47/48176* (2013.01); *B82Y 5/00* (2013.01); *C12N 9/96* (2013.01)

(58) Field of Classification Search
None
See application file for complete search history.

(56) References Cited

U.S. PATENT DOCUMENTS

| 6,506,577 B1 | 1/2003 | Deming et al. |
| 6,632,922 B1 | 10/2003 | Deming et al. |
| 6,686,466 B2 | 2/2004 | Zhao et al. |
| 6,818,732 B2 | 11/2004 | Deming et al. |

OTHER PUBLICATIONS

Fujita et al., Design of a Thermocontrollable Protein Complex, Bioconjugate Chemistry, 18(5): 1619-1624 (2007).
Kopecek et al., Hydrogels as Smart Biomaterials, Polymer International, 56(9):1078-1098 (2007).
Lu et al., Dextran-grafted-PNIPAAm as an Artificial Chaperone for Protein Refolding, Biochemical Engineering Journal, 27(3) 336-343 (2006).
Simnick et al., Biomedical and Biotechnological Applications of Elastin-Like Polypeptides, Polymer Reviews, 47(1): 121-154 (2007).
Thomas et al., Solid-state Nanostructured Materials from Self-assembly of a Globular Protein-polymer Diblock Copolymer, ACS Nano, 5(7):5697-5707 (2011).
International Search Report of PCT/US2011/057941, dated Mar. 14, 2012, 4 pages.
Written Opinion of PCT/US2011/057941, dated Mar. 14, 2012, 9 pages.
International Preliminary Report on Patentability for Application No. PCT/US2011/057941 mailed May 10, 2013.
Anderson et al., Materials science. Smart biomaterials. Science. Sep. 24, 2004;305(5692):1923-4. DOI:10.1126/science.1099987.
Bailon et al., PEG-modified biopharmaceuticals. Expert Opin Drug Deliv. Jan. 2009;6(1):1-16. doi: 10.1517/17425240802650568.
Becker et al., Peptide-Derivatized Shell-Cross-Linked Nanoparticles. 1. Synthesis and Characterization. Bioconjugate Chem. 2004, 15, 699-709.
Becker et al., Functionalized Micellar Assemblies Prepared via Block Copolymers Synthesized by Living Free Radical Polymerization upon Peptide-Loaded Resins. Biomacromolecules. 2005. 6: 220-228.
Bellomo et al., Stimuli-responsive polypeptide vesicles by conformation-specific assembly. Nat Mater. Apr. 2004;3(4):244-8. Epub Mar. 14, 2004.
Billot et al., Synthesis and structural study of block copolymers with a hydrophobic polyvinyl block and a hydrophilic polypeptide block: Copolymers polystyrene/poly(L-lysine) and polybutadiene/poly(L-lysine). Makromolekulare Chemie—Macromolecular Chemistry and Physics. Mar. 12, 1976. 177 (6): 1889-93. DOI: 10.1002/macp.1976.021770619.
Breedveld et al., Rheology of Block Copolypeptide Solutions: Hydrogels with Tunable Properties. Macromolecules. 2004. 37 (10): 3943-53.
Cavalcanti-Adam et al., Cell spreading and focal adhesion dynamics are regulated by spacing of integrin ligands. Biophys J. Apr. 15, 2007;92(8):2964-74. Epub Feb. 2, 2007.
Cavalcanti-Adam et al., Lateral spacing of integrin ligands influences cell spreading and focal adhesion assembly. European Journal of Cell Biology. May 2006. 85(3-4): 219-24. doi:10.1016/j.ejcb.2005.09.011.
Chécot et al., pH-responsive micelles and vesicles nanocapsules based on polypeptide diblock copolymers. Biomol Eng. Feb. 2007;24(1):81-5. Epub Jun. 3, 2006.
Chécot et al., Water-soluble stimuli-responsive vesicles from peptide-based diblock copolymers. Angew Chem Int Ed Engl. Apr. 15, 2002;41(8):1339-43. DOI: 10.1002/1521-3773(20020415)41:8<1339::AID-ANIE1339>3.0.CO;2-N.

(Continued)

*Primary Examiner* — Anand Desai
(74) *Attorney, Agent, or Firm* — Wolf, Greenfield & Sacks, P.C.

(57) ABSTRACT

The present disclosure provides protein-containing compositions, methods and uses thereof. A conjugate comprises a globular protein conjugated with a polymer that preserves the folded and functional structure of a protein. In some embodiments, a fusion protein comprises a globular protein conjugated with an elastin-mimic polymer (EMP). Also disclosed is an assembled solid-state or gel-state nanostructure comprising a plurality of conjugates, wherein each comprises a globular protein conjugated with a polymer that preserving the folded and functional structure of a protein. In certain embodiments, provided compositions and methods further comprise an additive.

18 Claims, 18 Drawing Sheets

(56) References Cited

OTHER PUBLICATIONS

Chen et al., Preparation and properties of thermoreversible, phase-separating enzyme-oligo(N-isopropylacrylamide) conjugates. Bioconjug Chem. Nov.-Dec. 1993 4(6):509-14.

Comisar et al., Engineering RGD nanopatterned hydrogels to control preosteoblast behavior: a combined computational and experimental approach. Biomaterials. Oct. 2007;28(30):4409-17. Epub Jul. 9, 2007.

Cracknell et al., Enzymes as working or inspirational electrocatalysts for fuel cells and electrolysis. Chem Rev. Jul. 2008;108(7):2439-61. doi: 10.1021/cr0680639.

Craighead et al., Chemical and topographical patterning for directed cell attachment. Current Opinion in Solid State and Materials Science. 2001. 5: 177-84.

Crespo et al., Small-Angle Neutron Scattering from Diblock Copolymer Poly(styrene-d8)-b-poly(ç-benzyl L-glutamate) Solutions: Rod-Coil to Coil-Coil Transition. Macromolecules. Feb. 2003. 36(4): 1253-6. DOI: 10.1021/ma021176j.

Dalby et al., Fibroblast reaction to island topography: changes in cytoskeleton and morphology with time. Biomaterials. Mar. 2003;24(6):927-35. doi:10.1016/S0142-9612(02)00427-1.

Danilov et al., (Arg-Gly-Asp)n-albumin conjugates as a model ubstratum for integrin-mediated cell adhesion. Exp Cell Res. May 1989;182(1):186-96. doi:10.1016/0014-4827(89)90290-5.

Das et al., Integration of Photosynthetic Protein Molecular Complexes in Solid-State Electronic Devices. Nano Letters 2004. 4(6): 1079-83.

De et al., Temperature-regulated activity of responsive polymer-protein conjugates prepared by grafting-from via RAFT polymerization. J Am Chem Soc. Aug. 27, 2008;130(34):11288-9. doi: 10.1021/ja804495v. Epub Jul. 30, 2008.

Deming, Facile synthesis of block copolypeptides of defined architecture. Nature. Nov. 27, 1997;390(6658):386-9. doi:10.1038/37084.

Dirks et al., Protein-Polymer Hybrid Amphiphiles. Advanced Materials. Sep. 22, 2008. 20(20): 3953-7. DOI: 10.1002/adma.200801383.

Duncan, The dawning era of polymer therapeutics. Nature Reviews Drug Discovery May 2003. 2(5): 347-60. doi:10.1038/nrd1088.

Engel et al., Nanotechnology in regenerative medicine: the materials side. Trends Biotechnol. Jan. 2008;26(1):39-47. Epub Nov. 26, 2007.

Flemming et al., Effects of synthetic micro- and nano-structured surfaces on cell behavior. Biomaterials. Mar. 1999;20(6):573-88.

Gallot, Comb-like and block liquid crystalline polymers for biological applications. Progress in Polymer Science. 1996. 21(6): 1035-88. doi:10.1016/S0079-6700(96)00010-X.

Glinel et al., Antibacterial and Antifouling Polymer Brushes Incorporating Antimicrobial Peptide. Bioconjugate Chemistry.Jan. 2009. 20(1): 71-7. DOI: 10.1021/bc800280u.

Goldberg et al., Nanostructured materials for applications in drug delivery and tissue engineering. J Biomater Sci Polym Ed. 2007. 18(3):241-68. DOI: 10.1163/156856207779996931.

Gregg et al., Redox polymer films containing enzymes. 1. A redox-conducting epoxy cement: synthesis, characterization, and electrocatalytic oxidation of hydroquinone. J. Phys. Chem. Jul. 1991. 95 (15): 5970-5975. DOI: 10.1021/j100168a046.

Hambourger et al., [FeFe]-hydrogenase-catalyzed H2 production in a photoelectrochemical biofuel cell. J Am Chem Soc. Feb. 13, 2008;130(6):2015-22. doi: 10.1021/ja077691k. Epub Jan. 19, 2008.

Heller, Electrical connection of enzyme redox centers to electrodes. Journal of Physical Chemistry. 1992. 96 (9): 3579-87.

Hoffman et al., Conjugates of stimuli-responsive polymers and proteins. Progress in Polymer Science. Aug.-Sep. 2007. 32 (8-9): 922-32.

Hoffman et al., Miyata T. Founder's Award, Society for Biomaterials. Sixth World Biomaterials Congress 2000, Kamuela, HI,May 15-20, 2000. Really smart bioconjugates of smart polymers and receptor proteins. J Biomed Mater Res. Dec. 15, 2000;52(4):577-86. DOI: 10.1002/1097-4636(20001215).

Hoffman, Bioconjugates of intelligent polymers and recognition proteins for use in diagnostics and affinity separations. Clin Chem. Sep. 2000;46(9):1478-86.

Huang et al., Myotube assembly on nanofibrous and micropatterned polymers. Nano Lett. Mar. 2006;6(3):537-42. DOI: 10.1021/nl060060o.

Karyakin et al., Hydrogen fuel electrode based on bioelectrocatalysis by the enzyme hydrogenase. Electrochem Commun 4:417-420. Electrochemistry Communications. May 2002. 4(5): 417-20. DOI: 10.1016/S1388-2481(02)00335-1.

Kay et al., Nanostructured polymer/nanophase ceramic composites enhance osteoblast and chondrocyte adhesion. Tissue Eng. Oct. 2002;8(5):753-61. doi:10.1089/10763270260424114.

Kessel et al., Mimicking biosilicification: programmed coassembly of peptide-polymer nanotapes and silica. Angew Chem Int Ed Engl. Oct. 24, 2007;46(47):9023-6.

Kiick, Biosynthetic Methods for the Production of Advanced Protein-Based Materials. Journal of Macromolecular Science, Part C: Polymer Reviews. 2007. 47(1): 1-7.

Kincaid et al., Entrapment of Photosystem I within Self-Assembled Films. Langmuir. Aug. 10, 2006. 22 (19): 8114-20. DOI: 10.1021/1a061326.

Kisiday et al., Self-assembling peptide hydrogel fosters chondrocyte extracellular matrix production and cell division: implications for cartilage tissue repair. Proc Natl Acad Sci U S A. Jul. 23, 2002;99(15):9996-10001. Epub Jul. 15, 2002. doi: 10.1073/pnas.142309999.

Klok et al., Biological-synthetic hybrid block copolymers: Combining the best from two worlds. Journal of Polymer Science Pad a-Polymer Chemistry. Jan. 1, 2005. 43(1): 1-17. DOI: 10.1002/pola.20527.

Koo et al., Co-regulation of cell adhesion by nanoscale RGD organization and mechanical stimulus. J Cell Sci. Apr. 1, 2002;115(Pt 7):1423-33.

Krassen et al., Immobilization of the [FeFe]-hydrogenase CrHydA1 on a gold electrode: design of a catalytic surface for the production of molecular hydrogen. J Biotechnol. Jun. 1, 2009;142(1):3-9. doi: 10.1016/j.jbiotec.2009.01.018. Epub Feb. 6, 2009.

Kukula et al., The formation of polymer vesicles or "peptosomes" by polybutadiene-block-poly(L-glutamate)s in dilute aqueous solution. J Am Chem Soc. Feb. 27, 2002;124(8):1658-63. DOI: 10.1021/ja0120911.

Kuwabata et al., Electrochemical conversion of carbon dioxide to methanol. Journal of the America Society 1994. 116,(12): 5437-43.

Laible et al., Electron-transfer dynamics of photosynthetic reaction centers in thermoresponsive soft materials. J Phys Chem B. Dec. 15, 2005;109(49):23679-86. E Pub Nov. 15, 2005. DOI: 10.1021/jp053884n.

Langer et al., Advances in biomaterials, drug delivery, and bionanotechnology. AIChe Journal. Dec. 2003. 49(12): 2990-3006. DOI: 10.1002/aic.690491202.

Lavan et al., Approaches for biological and biomimetic energy conversion. Proc Natl Acad Sci U S A. Apr. 4, 2006;103(14):5251-5. Epub Mar. 27, 2006. doi: 10.1073/pnas.0506694103.

Lecommandoux et al., Self-assembly of rod-coil diblock oligomers based on alpha-helical peptides. Macromolecules. 2001. 34(26): 9100-11.

Li et al., Biological response of chondrocytes cultured in three-dimensional nanofibrous poly(epsilon-caprolactone) scaffolds. J Biomed Mater Res A. Dec. 15, 2003;67(4):1105-14. DOI: 10.1002/jbm.A.10101.

Li et al., A three-dimensional nanofibrous scaffold for cartilage tissue engineering using human mesenchymal stem cells. Biomaterials. Feb. 2005;26(6):599-609. doi:10.1016/j.biomaterials.2004.03.005.

Li et al., Electrospun nanofibrous structure: a novel scaffold for tissue engineering. J Biomed Mater Res. Jun. 15, 2002;60(4):613-21.

Li et al., Multilineage differentiation of human mesenchymal stem cells in a three-dimensional nanofibrous scaffold. Biomaterials. Sep. 2005;26(25):5158-66. doi:10.1016/j.biomaterials.2005.01.002.

Lim et al., Cell sensing and response to micro- and nanostructured surfaces produced by chemical and topographic patterning. Tissue Eng. Aug. 2007;13(8):1879-91. E Pub Jun. 21, 2007. doi:10.1089/ten.2006.0154.

(56) References Cited

OTHER PUBLICATIONS

Liu et al., Nanomedicine for implants: a review of studies and necessary experimental tools. Biomaterials. Jan. 2007;28(2):354-69. doi:10.1016/j.biomaterials.2006.08.049.
Lutolf et al., Synthetic biomaterials as instructive extracellular microenvironments for morphogenesis in tissue engineering. Nat Biotechnol. Jan. 6, 2005. 23(1): 47-55. doi:10.1038/nbt1055.
Maheshwari et al., Cell adhesion and motility depend on nanoscale RGD clustering. J Cell Sci. May 2000;113 ( Pt 10):1677-86.
Mano et al., An electron-conducting cross-linked polyaniline-based redox hydrogel, formed in one step at pH 7.2, wires glucose oxidase. J Am Chem Soc. Jun. 6, 2007;129(22):7006-7. Epub May 11, 2007. DOI: 10.1021/ja071946c.
Nagapudi et al., Protein-Based Thermoplastic Elastomers. Macromolecules. 2005. 38(2): 345-54. DOI: 10.1021/ma0491199.
Nowak et al., Rapidly recovering hydrogel scaffolds from self-assembling diblock copolypeptide amphiphiles. Nature. May 23, 2002;417(6887):424-8.
Osada et al., Drug and gene delivery based on supermolecular assembly of PEG-polypeptide hybrid block copolymers. In Peptide Hybrid Polymers. Adv Polym Sci. Mar. 16, 2006. 202: 113-153. DOI: 10.1007/12_084.
Pennadam et al., Control of a multisubunit DNA motor by a thermoresponsive polymer switch. J Am Chem Soc. Oct. 20, 2004;126(41):13208-9. DOI: 10.1021/ja045275j.
Perly et al, Block copolymers polybutadiene/poly(benzyl-L-glutamate) and polybutadiene/poly(N5-hydroxypropylglutamine) preparation and structural study by X-ray and electron microscopy. Makromolekulare Chemie—Macromolecular Chemistry and Physics. Sep. 1976. 177 (9): 2569-89. DOI: 10.1002/macp.1976.021770901.
Petka et al., Reversible hydrogels from self-assembling artificial proteins. Science. Jul. 17, 1998;281(5375):389-92. DOI:10.1126/science.281.5375.389.
Reda et al., Reversible interconversion of carbon dioxide and formate by an electroactive enzyme. Proc Natl Acad Sci U S A. Aug. 5, 2008;105(31):10654-8. doi: .1073/pnas.0801290105. Epub Jul. 30, 2008.
Reynhout et al., Self-assembled architectures from biohybrid triblock copolymers. J Am Chem Soc. Feb. 28, 2007;129(8):2327-32. Epub Feb. 3, 2007. DOI: 10.1021/ja066790f.
Reynhout et al., Synthesis of polymer-biohybrids: from small to giant surfactants. Acc Chem Res. Jun. 16, 2009;42(6):681-92. doi:10.1021/ar800143a.
Rodríguez-Hernández et al., Reversible inside-out micellization of pH-responsive and water-soluble vesicles based on polypeptide diblock copolymers. J Am Chem Soc. Feb. 23, 2005;127(7):2026-7. DOI: 10.1021/ja043920g.
Sakiyama-Elbert et al., Functional Biomaterials: Design of Novel Biomaterials. J.A. Annual Review of Materials Research. Aug. 2001. 31: 183-201. DOI: 10.1146/annurev.matsci.31.1.183.
Satchi-Fainaro et al., Polymer therapeutic Current status and future challenges. In Polymer Therapeutics Ii: Polyme Conjugates and Gene Delivery Systems. Adv Polym. Sci. Nov. 10, 2006. 193: 1-65. DOI: 10.1007/12_024.
Schlaad et al., The role of chain-length distribution in the formation of solid-state structures of polypeptide-based rod-coil block copolymers. Macromolecules. 2004. 37 (6): 2210-4.
Schneider et al., Responsive hydrogels from the intramolecular folding and self-assembly of a designed peptide. J Am Chem Soc. Dec. 18, 2002;124(50):15030-7. DOI: 10.1021/ja027993g.
Shen et al., Tuning the erosion rate of artificial protein hydrogels through control of network topology. Nat Mater. Feb. 2006;5(2):153-8. Epub Jan. 29, 2006. doi:10.1038/nmat1573.
Shu et al., New design of helix bundle peptide-polymer conjugates. Biomacromolecules. Aug. 2008;9(8):2111-7. doi: 10.1021/bm800113g. Epub Jul. 16, 2008.
Soares et al., Antimicrobial peptide preferential binding of *E. coli* O157:H7. Protein Pept Lett. 2008. 15(10):1086-93. DOI: 10.2174/092986608786071049#sthash.EK8W4KAY.dpuf.

Stayton et al., Control of protein-ligand recognition using a stimuli-responsive polymer. Nature. Nov. 30, 1995;378(6556):472-4.
Stevens et al., Exploring and engineering the cell surface interface. Science. Nov. 18, 2005;310(5751):1135-8. DOI:10.1126/science.1106587.
Storrie et al., Supramolecular crafting of cell adhesion. Biomaterials. Nov. 2007;28(31):4608-18.
Teixeira et al., The effect of environmental factors on the response of human corneal epithelial cells to nanoscale substrate topography. Biomaterials. Jul. 2006;27(21):3945-54. Epub Mar. 30, 2006.
Urry et al., Temperature of polypeptide inverse temperature transition depends on mean residue hydrophobicity. J. Am. Chem. Soc. May 1991. 113(11): 4346-8. DOI: 10.1021/ja00011a057.
Uzarski et al., The effects of solution structure on the surface conformation and orientation of a cysteine-terminated antimicrobial peptide cecropin P1. Colloids and Biointerfaces. Dec. 1, 2008. 67 (2): 157-65. doi:10.1016/j.colsurfb.2008.07.011.
Van Hest, Biosynthetic-Synthetic Polymer Conjugates. Journal of Macromolecular Science. Part C:Polymer Reviews. 2007. 47(1): 63-92.
Vandermeulen et al., PEG-based hybrid block copolymers containing alpha-helical coiled coil peptide sequences: Control of self-assembly and preliminary biological evaluation. Macromolecules. Jan. 11, 2005. 38(3): 761-769. DOI: 10.1021/ma0485538.
Vandermeulen et al., Structure and dynamics of self-assembled poly(ethylene glycol) based coiled-coil nano-objects. Chemphyschem. Apr. 19, 2004;5(4):488-94. DOI: 10.1002/cphc.200301079.
Wilkinson et al., The use of materials patterned on a nano- and micro-metric scale in cellular engineering. Materials Science & Engineering C—Biomimetic and Supramolecular Systems. Current Trends in Nanotechnologies: From Materials to Systems, Proceedings of Symposium S, EMRS Spring Meeting 2001, Strasbourg France. Jan. 2, 2002. 19 (1-2): 263-9. doi:10.1016/S0928-4931(01)00396-4.
Wilkinson et al., Nanofabrication in cellular engineering. J. Vac. Sci. Technol B. 1998. 16(6): 3132-6.
Willner et al., Integration of Layered Redox Proteins and Conductive Supports for Bioelectronic Applications. Angew Chem Int Ed Engl. Apr. 2000;39(7):1181-1218.
Willner et al., Electron-transfer communication between a redox polymer matrix and an immobilized enzyme: activity of nitrate reductase in a viologen-acrylamide copolymer. Journal of the American Chemical Society. Aug. 1990. 112(17): 6438-9. DOI: 10.1021/ja00173a065.
Wright et al., Thermoplastic Elastomer Hydrogels via Self-Assembly of an Elastin-Mimetic Triblock Polypeptide. Adv. Funct Mater. Feb. 2002. 12(2): 149-54. DOI: 10.1002/1616-3028(20020201)12:23.0.CO;2-N.
Wright et al., Self-assembly of block copolymers derived from elastin-mimetic polypeptide sequences. Adv Drug Deliv Rev. Oct. 18, 2002. 54(8): 1057-73. doi:10.1016/S0169-409X(02)00059-5.
Xu et al., Genetically engineered block copolymers: influence of the length and structure of the coiled-coil blocks on hydrogel self-assembly. Pharm Res. Mar. 2008;25(3):674-82. Epub Aug. 23, 2007.
Xu et al., Reversible hydrogels from self-assembling genetically engineered protein block copolymers. Biomacromolecules. May-Jun. 2005;6(3):1739-49. DOI: 10.1021/bm050017f.
Xu et al., Coiled-coil helix bundle, a peptide tertiary structural motif toward hybrid functional materials. Soft Matter. Oct. 16, 2010. 6(2): 212-7. DOI: 10.1039/B914565F.
Yokoyama et al., Characterization of physical entrapment and chemical conjugation of adriamycin in polymeric micelles and their design for in vivo delivery to a solid tumor. Journal of Controlled Release 1998. 50 (1-3): 79-92. doi:10.1016/S0168-3659(97)00115-6.
Yokoyama et al., Preparation of micelle-forming polymer-drug conjugates. Bioconjugate Chemistry. Jul. 1992. 3(4): 295-301. DOI: 10.1021/bc00016a007.
Zhang, Fabrication of novel biomaterials through molecular self-assembly. Nature Biotechnology 2003. 21(10): 1171-1178 . E Pub Sep. 30, 2003. doi:10.1038/nbt874.

```
                        SEQUENCE LISTING

<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: artificial protein polymer sequence
<220> FEATURE:
<221> NAME/KEY: misc_feature
<222> LOCATION: (4)..(4)
<223> OTHER INFORMATION: Gly
<220> FEATURE:
<221> NAME/KEY: misc_feature
<222> LOCATION: (4)..(4)
<223> OTHER INFORMATION: Xaa = Val, Leu, Ile, Ala or Gly

<400> SEQUENCE: 1

Val Pro Gly Xaa Gly
1               5

<210> SEQ ID NO 2
<211> LENGTH: 250
<212> TYPE: PRT
<213> ORGANISM: Artificial Sequence
<220> FEATURE:
<223> OTHER INFORMATION: artificial protein polymer sequence

<400> SEQUENCE: 2

Val Gly Val Pro Gly Val Gly Val Pro Gly Gly Gly Val Pro Gly Ala
1               5                   10                  15

Gly Val Pro Gly Val Gly Val Pro Gly Val Gly Val Pro Gly Val Gly
                20                  25                  30

Val Pro Gly Gly Gly Val Pro Gly Ala Gly Val Pro Gly Gly Gly Val
            35                  40                  45

Pro Gly Val Gly Val Pro Gly Val Gly Val Pro Gly Gly Gly Val Pro
    50                  55                  60

Gly Ala Gly Val Pro Gly Val Gly Val Pro Gly Val Gly Val Pro Gly
65                  70                  75                  80

Val Gly Val Pro Gly Gly Gly Val Pro Gly Ala Gly Val Pro Gly Gly
                85                  90                  95

Gly Val Pro Gly Val Gly Val Pro Gly Val Gly Val Pro Gly Gly Gly
                100                 105                 110

Val Pro Gly Ala Gly Val Pro Gly Val Gly Val Pro Gly Val Gly Val
            115                 120                 125

Pro Gly Val Gly Val Pro Gly Gly Gly Val Pro Gly Ala Gly Val Pro
    130                 135                 140

Gly Gly Gly Val Pro Gly Val Gly Val Pro Gly Val Gly Val Pro Gly
145                 150                 155                 160

Gly Gly Val Pro Gly Ala Gly Val Pro Gly Val Gly Val Pro Gly Val
                165                 170                 175

Gly Val Pro Gly Val Gly Val Pro Gly Gly Gly Val Pro Gly Ala Gly
                180                 185                 190

Val Pro Gly Gly Gly Val Pro Gly Val Gly Val Pro Gly Val Gly Val
            195                 200                 205

Pro Gly Gly Gly Val Pro Gly Ala Gly Val Pro Gly Val Gly Val Pro
    210                 215                 220
```

-continued

```
Gly Val Gly Val Pro Gly Val Gly Val Pro Gly Gly Gly Val Pro Gly
225                 230                 235                 240

Ala Gly Val Pro Gly Gly Gly Val Pro Gly
                245                 250
```

US 9,359,457 B2

PROTEIN-BASED CONJUGATES AND SELF-ASSEMBLED NANOSTRUCTURES

CROSS REFERENCES OF RELATED APPLICATIONS

The present application is a 35 U.S.C. 371 National Stage of International Application No. PCT/US2011/057941, filed Oct. 26, 2011, which claims the benefit of a U.S. provisional patent application Ser. No. 61/406,623, filed Oct. 26, 2010, the contents of which are incorporated herein by reference.

SEQUENCE LISTING

In accordance with 37 CFR 1.52(e)(5), the present specification makes reference to a Sequence Listing submitted electronically in the form of an ASCII text file (entitled "Sequence_Listing.txt" created on Jul. 8, 2013 and 6 kilobytes in size). The entire contents of the Sequence Listing are herein incorporated by reference, with the intention that, upon publication (including issuance), this incorporated sequence listing will be inserted in the published document immediately before the claims.

BACKGROUND

Protein-based materials have attracted a great deal of interest as both bioactive and bioelectronic materials. In addition, it has become increasingly clear over the last decade that control over biological functionality is critical to controlling the interface of biomaterials with living systems. The presentation of protein signals that aid or deter cell adhesion, differentiation, growth, and migration is critical to enhancing wound healing, controlling stem cell behaviors, and synthesizing robust antimicrobial surfaces. It has also been demonstrated that both the microscale and nanoscale spatial arrangement of these factors have a large impact on the elicited biological response, motivating the desire to produce self-assembled nanostructures from these materials, including nanopatterned surfaces and fibrillar tissue engineering matrices.

A number of approaches have also been pursued to develop nanostructured proteins for biosensors and bioelectronics, but none of these devices achieve the ideal combination of transport properties, control of protein orientation, and nano scale spatial control in either two or three dimensions. For example, surface nanopatterning based on the attachment of proteins to chemically inhomogeneous surfaces has been used as one method of promoting focal adhesion formation. Nanoscale topographical patterns of posts or lines have also been prepared by photolithography, but those lithography steps are costly and their ability to pattern on very short length scales is limited. To go beyond two-dimensional nanostructures, electrospun nanofiber scaffolds, self-assembled peptide nanofiber scaffolds, nanocomposites, and collagen fiber matrices have been investigated, but none of these materials produces a regularly ordered nanostructure.

Therefore, there remains a need in the art for protein-based materials, in particular, those can produce well-controlled three-dimensional nanostructures.

SUMMARY

The present disclosure provides at least compositions and methods for nanopatterning or nanostructuring of conjugated proteins, in particular, a globular protein, in a solid or gel state. In some embodiments, a conjugate comprises a globular protein conjugated, covalently or non-covalently, with a polymer that preserves the folded and functional structure of a protein. In some embodiments, a fusion protein comprises a globular protein conjugated with an elastin-mimic protein (EMP). Such conjugates including fusion proteins can be self-assembled to produce nanostructures in a solid state, either with no or limited solvent, or in a gel state, where the specific structure of the nanostructures may be controlled through the choice of protein, polymer chemistry, polymer molecular weight, polymer attachment site, and processing technique used to induce self-assembly. In certain embodiments, such assembled nanostructures further comprise an additive. Methods may be applied to nanopatterning thin films and interfaces as well as producing nanostructured protein-containing materials.

BRIEF DESCRIPTION OF THE DRAWING

The drawings are for illustrative purposes only, not for limitation.

DEFINITIONS

Figure 1:
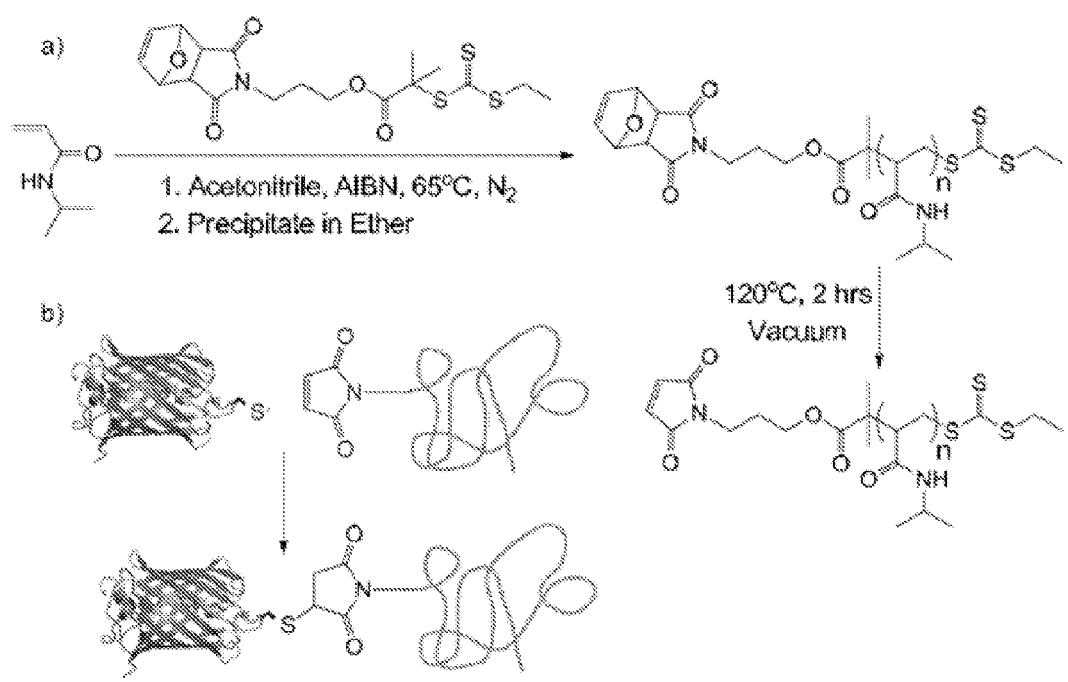
FIG. 1 illustrates a schematic of the synthesis of maleimide-functionalized poly(N-isopropylacrylamide) (PNIPAM) and its conjugation to mCherryS131C to create a protein-polymer diblock copolymer.

In order for the present invention to be more readily understood, certain terms are first defined below. Additional definitions for the following terms and other terms are set forth throughout the specification.

"Conjugated": As used herein, the terms "conjugated", "associated", "attached", "complexed", "linked", and "tethered," and grammatical equivalents, typically refer to two or more moieties connected with one another, either directly or indirectly (e.g., via one or more additional moieties that serve as a linking agent), to form a structure that is sufficiently stable so that the moieties remain connected under the conditions in which the structure is used, e.g., physiological conditions. In some embodiments, the moieties are attached to one another by one or more covalent bonds. In some embodiments, the moieties are attached to one another by a mechanism that involves specific (but non-covalent) binding (e.g. streptavidin/avidin interactions, antibody/antigen interactions, etc.). Alternatively or additionally, a sufficient number of weaker interactions (non-covalent) can provide sufficient stability for moieties to remain connected. Exemplary non-covalent interactions include, but are not limited to, affinity interactions, metal coordination, physical adsorption, host-guest interactions, hydrophobic interactions, pi stacking interactions, hydrogen bonding interactions, van der Waals interactions, magnetic interactions, electrostatic interactions, dipole-dipole interactions, etc.

"Biocompatible": The term "biocompatible", as used herein is intended to describe materials that do not elicit a substantial detrimental response in vivo, preserve the folded and functional structure of a protein, or both. In some embodiments, a substance is considered to be "biocompatible" if its addition to cells in vitro or in vivo results in less than or equal to about 50%, about 45%, about 40%, about 35%, about 30%, about 25%, about 20%, about 15%, about 10%, about 5%, or less than about 5% cell death.

"Biodegradable": As used herein, the term "biodegradable" refers to substances that are degraded under physiological conditions. In some embodiments, a biodegradable substance is a substance that is broken down by cellular machinery. In some embodiments, a biodegradable substance is a substance that is broken down by chemical processes.

"Polymer": As used herein, the term "polymer" generally refers to a large molecule composed of repeating structural units, typically connected to each other by covalent bonds. Polymers can be natural and/or synthetic materials with a wide variety of properties. In some embodiments, a polymer used in the present application can be a synthetic material. In certain embodiments, a synthetic polymer comprises a carbon backbone. For example, a synthetic polymer can be plastics and/or elastomers. In some embodiments, a polymer can be a natural biopolymer such as nucleic acids and proteins. In certain embodiments, a polymer can be an elastin-mimic polymer (EMP).

"Polypeptide" or "peptide": According to the present application, a "polypeptide" or "peptide" comprises a string of at least three amino acids linked together by peptide bonds. The terms may be used interchangeably. As appreciated by a person with ordinary skill in the art, peptides are distinguished from proteins on the basis of size, folding ability, activity, etc.

"Protein": As used herein, the term "protein" generally refers to compounds consisting of one or more polypeptides arranged in a biologically functional way. Typically, proteins are folded into a globular or fibrous form.

DETAILED DESCRIPTION OF CERTAIN EMBODIMENTS

A. Conjugates and Assemblies

The present disclosure, among other things, provides compositions comprising a globular protein conjugated with a polymer that preserves the folded and functional structure of a protein. In general, compositions of the invention include a conjugate and its self-assembled nanostructure. Proteins/polymers are typically selected to construct such a conjugate, so that it self assembles into a three-dimensional nanostructure. Such nanostructures advantageously achieve a relatively high density of proteins, thereby allowing the nanostructures to have functions such as increased enzymatic activity or detectable signal (e.g., fluorescence) per unit volume.

Compositions of the invention include a conjugate comprising a globular protein conjugated with a polymer that preserves the folded and functional structure of a protein. In some embodiments, a conjugate can be a fusion protein comprising a globular protein conjugated with an elastin-mimic polymer (EMP) or other proteins with a Gaussian coil configuration. Such a "coil" protein typically provides structural and mechanical properties, while a globular protein serves as a functional protein in the fusion protein.

Globular Proteins

Globular proteins are folded structures and can be relatively spherical in shape. Globular proteins include proteins that are more or less soluble in aqueous solutions. There may be a single chain or two or more chains folded together. Portions of the chains may have helical structures, pleated structures, or completely random structures. In some embodiments, a globular protein can be an enzyme. Exemplary globular proteins include, but are not limited to, hemoglobin, myoglobin, green fluorescent protein (GFP), enhanced GFP (EGFP), lysozyme, albumin (such as bovine serum albumin, BSA), and carbonic anhydrase. In some embodiments, a globular protein can be mCherry, as illustrated in the Examples below.

A globular protein generally has a larger molecular weight than a simple peptide or a polypeptide. In some embodiments, the molecular weight of a globular protein is greater than 10 kDa. In some embodiments, the molecular weight of a globular protein is greater than 20 kDa, 30 kDa, or 50 kDa. In some embodiments, the molecular weight of a globular protein may be greater than 100 kDa. In some embodiments, the molecular weight of a globular protein ranges from about 10 kDa to about 5000 kDa. In some embodiments, the molecular weight of a globular protein may range from about 50 kDa to 500 kDa. In some embodiments, the molecular weight of a globular protein may range from about 50 kDa to 200 kDa. In some embodiments, the molecular weight of a globular protein may range from about 50 kDa to 100 kDa.

The amount of globular protein in a conjugate and/or its assembled nanostructure may be chosen to achieve a desired density/weight percentage. In some embodiments, the weight percentage of a globular protein may be greater than about 20%, about 30%, about 35%, about 40%, about 45%, about 50%, about 55%, about 60%, about 65%, about 70%, about 75%, about 80%, or about 85%. In some embodiments, the weight percentage of a globular protein may be less than about 90%, about 85%, about 80%, about 75%, about 70%, about 65%, about 60%, about 55%, about 50%, about 45%, about 40%, or about 35%. In some embodiments, the weight percentage of a globular protein may range from about 20% to about 85%, from about 30% to about 70%, from about 40% to about 60% or between any other pair of boundaries provided above.

Polymers

In general, any polymers that can preserve the folded and functional structure of a protein can be used in accordance with the present disclosure. In certain embodiments, the polymer is selected such that it does not interfere with a protein's structure and/or activity by more than 50%, 40%, 30%, 20% or 10% over a time period relevant to the conjugated prepared, which could be one minute (or less), one hour, one day, one week, one month, one year or longer. Protein structure can be measured using standard methods such as circular dichroism, UV-visible spectroscopy, NMR, x-ray crystallography, and small angle x-ray scattering and assessing how much protein retains the same structure as at the time of synthetic.

Polymers may be homopolymers or copolymers comprising two or more monomers. In terms of sequence, copolymers may be block copolymers, graft copolymers, random copolymers, blends, mixtures, and/or adducts of any of the foregoing and other polymers. Typically, polymers in accordance with the present invention are organic polymers and contain a carbon backbone.

By tailoring their molecular architecture, a polymer used in accordance with the present application can be designed and selected to have especially desirable properties. For example, glass transition temperature is a temperature at which a materials (e.g., a polymer) changes from a hard and relatively brittle state into a molten state. The glass transition temperature (Tg) of a polymer used in accordance with the present application can be in a range that does not denature a protein. In some embodiments, the Tg of a polymer is greater than 0° C., 10° C., 20° C., 25° C., 30° C., 37° C. (approximately human body temperature), 40° C., 50° C., 60° C., or 70° C. In some embodiments, the Tg of a polymer is less than 80° C., 70° C., 60° C., 50° C., 40° C., 37° C. (approximately human body temperature), 30° C., 25° C., 20° C., or 10° C. In some embodiments, the Tg of a polymer ranges from 0° C. to 80° C., from 25° C. to 70° C., or from 37° C. to 50° C. Without being bound to any particular theory, compositions comprising a globular protein conjugated with a polymer may have a similar Tg as that of the polymer.

In general, the lower critical solution temperature (LCST) refers to the critical temperature below which the components of a mixture are miscible for all compositions. The LCST of a conjugate in a solution can refer to the LCST of the polymer or the protein of a conjugate disclosed herein. The LCST of a conjugate in a solution can be in a range that does not denature a protein. In some embodiments, the LSCT of the conjugate used in accordance with the present application is greater than 0° C., 10° C., 20° C., 25° C., 30° C., 37° C. (approximately human body temperature), 40° C., 50° C., 60° C., or 70° C. In some embodiments, the LSCT is less than 80° C., 70° C., 60° C., 50° C., 40° C., 37° C. (approximately human body temperature), 30° C., 25° C., 20° C., or 10° C. In some embodiments, the LSCT ranges from 0° C. to 80° C., from 25° C. to 70° C., or from 37° C. to 50° C.

In some embodiments, polymers may be biocompatible. In some embodiments, polymers may be biodegradable. In some embodiments, polymers may be both biocompatible and biodegradable.

Suitable polymers generally include hydrophilic and hydrophobic regions. Hydrophobic regions can, for example, be associated with a carbon backbone. Hydrophilic regions can, for example, be associated with sidechains containing hydroxyl, carboxylic acid, amide, amine and/or ammonium groups.

In some embodiments, polymers may be modified with one or more moieties and/or functional groups. Any moiety or functional group can be used in accordance with the present invention. In some embodiments, polymers may be modified with polyethylene glycol (PEG), with a carbohydrate, and/or with acyclic polyacetals derived from polysaccharides.

A polymer used in accordance with the present application can have a wide range of molecular weights. In some embodiments, the molecular weight of a polymer is greater than 5 k.

In some embodiments, the molecular weight of a polymer is greater than 10 k. In some embodiments, the molecular weight of a polymer is greater than 50 k. In some embodiments, the molecular weight of a polymer ranges from about 5 k to about 100 k. In some embodiments, the molecular weight of a polymer ranges from about 10 k to 50 k.

In general, the weight percentage of a polymer can be selected to achieve a desired density and/or activity of the globular protein. In some embodiments, the weight percentage of a polymer may be greater than about 20%, about 30%, about 35%, about 40%, about 45%, about 50%, about 55%, about 60%, about 65%, about 70%, about 75%, about 80%, or about 85%. In some embodiments, the weight percentage of polymer may be less than about 90%, about 85%, about 80%, about 75%, about 70%, about 65%, about 60%, about 55%, about 50%, about 45%, about 40%, or about 35%. In some embodiments, the weight percentage of a polymer may range from about 20% to about 85%, from about 30% to about 70%, from about 40% to about 60% or between any other pair of boundaries provided above.

Natural Polymers

In some embodiments, a polymer may be a natural polymer, such as a carbohydrate, protein, nucleic acid, lipid, etc. In some embodiments, natural polymers may be synthetically manufactured.

In some embodiments, a polymer may be a structural protein or peptide that provide mechanic properties such as elasticity and plasticity. Exemplary proteins that may be used in accordance with the present invention include, but are not limited to, elastin, fibrin, albumin, poly(amino acids) (e.g., polylysine), glycoproteins, antibodies, etc.

In some embodiments, such a structural protein or peptide can be derived from the sequence of a protein. Proteins may contain L-amino acids, D-amino acids, or both and may contain any of a variety of amino acid modifications or analogs known in the art. Useful modifications may include, e.g., terminal acetylation, amidation, lipidation, phosphorylation, glycosylation, acylation, farnesylation, sulfation, etc.

In some embodiments, polymers can be protein polymers such as elastin-mimic polymers (EMP). As well known in the art, protein polymers derived from elastin-mimetic peptide sequences can be synthesized with well control of macromolecular architecture using genetic engineering techniques (E. R. Wright et al., *Advanced Drug Delivery Review*, 54 (2002) 1057-1073 and D. W. Urry et al., *J. Am. Chem. Soc.*, 1991, 113, 4346-4348, the contents of which are incorporated herein by reference). In certain embodiments, an EMP can be a polymer comprising repeat units of a five-amino acid consensus sequence, wherein the first and fourth amino acids can independently be Val, Leu or Ile, the second amino acid can be Pro, the third and the fifth amino acids can independently be Gly or Ala. In certain embodiments, an EMP can comprise a repeat unit of VPGXG (SEG ID No:1), where X can be any amino acid, including V, L, I, A and G. In some embodiments, an EMP is a protein polymer whose amino acid sequence shows contains at least 60%, 65%, 70%, 75%, 80%, 85%, 90%, 95%, 98%, 99%, or 100% of its sequence with one or more of the five-amino acid consensus sequence repeat units. A specific example of a repeat unit is VPGXG (SEG ID No:1), where X is V, A, or G in a ratio of 5:2:3. More specifically, an EMP can comprise a sequence of (SEG ID No: 2)
vgvpgvgvpgggvpgagvpgvgvpgvgvpgvgvpgggvpgagvpgggv pgvgvpgvgvpgggvpgagvpgvgvpgvgvpgvgvpgggvpgagvpgggv pgvgvpgvgvpgggvpgagvpgvgvpgvgvpgvgvpgggvpgagvpgggv -continued
pgvgvpgvgvpgggvpgagvpgvgvpgvgvpgvgvpgggvpgagvpgggv pgvgvpgvgvpgggvp-
gagvpgvgvpgvgvpgvgvpgggvpgagvpgggvpg.

Synthetic Polymers

In some embodiments, polymers may be synthetic polymers, including, but not limited to, polyethylenes, polycarbonates (e.g. poly(1,3-dioxan-2-one)), polyanhydrides (e.g. poly(sebacic anhydride)), polyhydroxyacids (e.g. poly(β-hydroxyalkanoate)), polypropylfumarates, polycaprolactones, polyamides (e.g. polycaprolactam), polyacetals, polyethers, polyesters (e.g. polylactide, polyglycolide), poly(orthoesters), polycyanoacrylates, polyvinyl alcohols, polyurethanes, polyphosphazenes, polyacrylates, polymethacrylates, polyureas, polystyrenes, and polyamines. In some embodiments, polymers include polymers which have been approved for use in humans by the U.S. Food and Drug Administration (FDA) under 21 C.F.R. §177.2600, including, but not limited to, polyesters (e.g. polylactic acid, poly(lactic-co-glycolic acid), polycaprolactone, polyvalerolactone, poly(1,3-dioxan-2-one)); polyanhydrides (e.g. poly(sebacic anhydride)); polyethers (e.g., polyethylene glycol); polyurethanes; polymethacrylates; polyacrylates; polycyanoacrylates; copolymers of PEG and poly(ethylene oxide) (PEO). Exemplary synthetic polymers suitable for use in accordance with the present application include, but are not limited to, poly(N-isopropylacrylamide) (NIPAM), poly(3-[N-(2-methacroyloyethyl)-N,N-dimethylammonio]propane-sulfonate), poly (hydroxypropyl acrylate), poly(ethylene glycol methyl ether acrylate-b-methoxyethoxy ethyl acrylate) and any combination thereof. For example, copolymers comprising NIPAM and N-tert-butylacrylamide can be suitable for use.

In some embodiments, polymers are hydrophilic. For example, polymers may comprise anionic groups (e.g. phosphate group, sulphate group, carboxylate group); cationic groups (e.g. quaternary amine group); or polar groups (e.g. hydroxyl group, thiol group, amine group).

In some embodiments, polymers are chemically neutral. Neutral synthetic polymers can be generated from derivatives of poly(ethylene glycol) (PEG), poly(hydroxyethyl methacrylate) (PHEMA), and poly(vinyl alcohol) (PVA).

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and combinations comprising one or more of the foregoing polymers. An acrylic polymer may comprise fully-polymerized copolymers of acrylic and methacrylic acid esters with a low content of quaternary ammonium groups.

PEGs may be useful, in some embodiments, in accordance with the present application since they are nontoxic, non-immunogenic, inert to most biological molecules (e.g. proteins), and approved by the FDA for various clinical uses. PEG polymers can be covalently crosslinked using a variety of methods to form hydrogels. In some embodiments, PEG chains are crosslinked through photopolymerization using acrylate-terminated PEG monomers. In addition to chemical modification, block copolymers of PEG, such as triblock copolymers of PEO and poly(propylene oxide) (henceforth designated as PEO-b-PPO-b-PEO), degradable PEO, poly (lactic acid) (PLA), and other similar materials, can be used to add specific properties to the PEG.

Poly(hydroxyethyl methacrylate) (PHEMA) may be useful in some embodiments. It is characterized by desirable mechanical properties, optical transparency, and stability in water. Like PEG, various modifications can be made to PHEMA derivatives to modify its properties. Copolymerization of HEMA monomers with other monomers, such as methyl methacrylate, can be used to modify properties such as swelling and mechanical properties.

In some embodiments, polymers may be polyesters, including copolymers comprising lactic acid and glycolic acid units, such as poly(lactic acid-co-glycolic acid) and poly (lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; copolymers of PEG and copolymers of lactide and glycolide (e.g. PLA-PEG copolymers, PGA-PEG copolymers, PLGA-PEG copolymers, and derivatives thereof. In some embodiments, polyesters include, for example, polyanhydrides, poly(ortho ester), poly(ortho ester)-PEG copolymers, poly(caprolactone), poly(caprolactone)-PEG copolymers, polylysine, polylysine-PEG copolymers, poly(ethylene imine), poly(ethylene imine)-PEG copolymers, poly(L-lactide-co-L-lysine), poly(serine ester), poly(4-hydroxy-L-proline ester), poly[α-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid: glycolic acid ratio. In some embodiments, PLGA to be used in accordance with the present invention is characterized by a lactic acid:glycolic acid ratio of approximately 85:15, approximately 75:25, approximately 60:40, approximately 50:50, approximately 40:60, approximately 25:75, or approximately 15:85.

According to the present application, provided conjugates including fusion proteins, which comprises a globular protein conjugated with a polymer that preserves the folded and functional structure of a protein, can self assembled into a solid-state or gel-state nanostructure.

Additives

In some embodiments, such assembled nanostructures further comprise one or more additives. It is recognized in the present application that additives such as certain small molecules can improve the activity and/or stability of the globular protein in the assembled nanostructure.

Without being bound to any particular theory, typical additives are capable of both donating and accepting hydrogen bonds. Additives suitable for use in accordance with the present application generally fall into three main categories: sugars, hydroxyl-containing compounds, and polymeric hydrogen bonding additives. Example of sugars include trehalose and sucrose. Examples of hydroxyl-containing compounds are typically water-soluble compounds such as diols and polyols (e.g., glycerol, ethylene glycol and PEG including oligoPEGs). In certain embodiments, water can be used an additive when an aqueous solution contains a miscible co-solvent. Examples of polymers capable of hydrogen bonding include poly(hydroxyl ethyl methacrylate) and poly(vinyl alcohol), including when such polymers have an average molecular weight of 0.5-1000 kDa, 1-100 kDa, or 1-10 kDa. In some embodiments, an additive used in accordance with the present application can be any combination of one or more additives.

Generally speaking, the mixture of a conjugate in an aqueous solution in accordance with the present application contains a small amount of additive. In some embodiments, the weight percentage of an additive in the mixture is greater than 2%, 10%, 20%, 30%, 40%, 50%, 60% or even 70% relative to the mass of the conjugate. In some embodiments, the weight percentage of an additive in the mixture is less than 80%, 70%, 60%, 50%, 40%, 30%, 20%, 10%, or 5%. In some embodiments, the weight percentage of an additive ranges from 2% to 60%, 10% to 50% or 20%-40%.

Solid-state or gel-state nanostructures assembled in accordance with the present application advantageoulsly maintain the activity of the protein. In particular, provided nanostructures assembled with additives surprisingly maintain similar or even higher activity of the protein as compared to those without additives.

In some embodiments, solid-state or gel-state nanostructures assembled from conjugates comprising a globular protein conjugated with a polymer maintain at least 20%, 30%, 35%, 40%, 50%, 55%, 60%, 65%, 70%, 75%, 80%, 85%, 90%, 95% or even 100% of the activity (e.g., enzymatic activity, fluorescence) and/or structure of the globular protein as compared to the globular protein not conjugated to the polymer. In some embodiments, solid-state or gel-state nanostructures assembled from provided conjugates comprising a globular protein conjugated with a polymer can maintain 20% to 70%, or 30% to 65% activity of the globular protein as compared to the globular protein not conjugated to the polymer.

B. Methods

Based upon the description provided herein, conjugates provided in the present application can be prepared using the selected polymers and globular proteins using methods well known in the art. More generally, a variety of methods for synthesizing suitable polymers are described in *Concise Encyclopedia of Polymer Science and Polymeric Amines and Ammonium Salts*, Ed. by Goethals, Pergamon Press, 1980; *Principles of Polymerization* by Odian, John Wiley & Sons, Fourth Edition, 2004; *Contemporary Polymer Chemistry* by Allcock et al., Prentice-Hall, 1981; Deming et al., 1997, *Nature*, 390:386; and in U.S. Pat. Nos. 6,506,577, 6,632,922, 6,686,446, and 6,818,732.

In general, such conjugates can be prepared in an aqueous solution, followed by removing the aqueous solution (e.g., water or other solvents) so that the conjugates self-assemble to form a solid-state or gel-state nanostructure. Removing can be done by evaporating, filtering, or other techniques known in the art. In certain embodiments, removing (e.g., evaporating) can be done under vacuume or under a certain pressure.

In some embodiments, methods of preparing assembled nanostructures further comprises a step of adding an additive as discussed above before the step of removing an aqueous solution. In some embodiments, methods further comprises a step of solvent annealing after the step of removing.

In some embodiments, such as when a non-selective solvent is used, the methods herein are conducted at a temperature lower than the LSCT of a conjugate in a solution. In some embodiments, such as when a selective solvent is used, the methods herein are conducted at a temperature at or above the LSCT. In certain embodiments, the methods herein are conducted at a temperature at or above the LSCT of the polymer of a conjugate, and the solvent used is a polymer selective solvent. In certain embodiments, the methods herein are conducted at a temperature at or above the LSCT of the protein of a conjugate, and the solvent used is a protein selective solvent.

C. Applications

In general, compositions and methods described herein may be used to produce protein-based materials. By selectively choosing the polymers and proteins in the conjugates and the processing conditions, well-controlled protein density and structure (e.g., nanopattern) can be achieved for a variety of applications.

In some embodiments, compositions described herein can be useful as bioactive materials. Bioactive materials have been widely investigated for the formation of micelles or vesicles to deliver therapeutic agents, such as antimicrobial materials, biomineralization materials and to supply deficient proteins. In certain embodiments, the conjugates can be used in drug delivery applications. In certain embodiments, the conjugates and methods described herein can be applied to modulate protein binding coefficients or enzyme activity in self-assembled nanostructures useful for nanopatterned surfaces, tissue engineering matrices, etc. In certain embodiments, the conjugates can be used as biocatalysts or biosensors, which preserve the bioactivity of proteins such as enzymes.

In some embodiments, the compositions can be useful as bioelectronic materials. Assembled nanostructures with optical or electronic functionality are of great interest for a variety of bioelectronic devices, including photovoltaic cells, catalysts for hydrogen production or carbon dioxide reduction, biosensors, and biofuel cells. These bioelectronic materials offer potential advantages over synthetic catalysts and optoelectronics by using highly evolved proteins that may exceed the selectivity, efficiency, and transformation rate of synthetic materials. In certain embodiments, the conjugates and methods described herein can be used in engineering devices containing active proteins, such as to provide control over multiple phases for the transport of charges and reagents, provide orientation of the protein at an interface, and/or provide structure of the material in three dimensions to achieve a high protein density at the interface.

Enzymes, in some embodiments, can be useful in accordance with the present application, because they are known for a number of advantages including substrate specificity, high catalytic rate, mild operating conditions, biodegradability and renewability, and the capability to operate on non-traditional substrates. In certain embodiments, by using enzymes in provided compositions, enzymes can be incorporated into devices such as sensors for chemical and bio warfare agents, biofuel cells, carbon sequestration, and photovoltaics. For example, compositions provided herein containing enzymes can be used to construct fuel cells. Such fuel cells would not require the bulky electrolyte membrane needed for traditional fuel cells, making these enzymatic devices considerably lighter and smaller than what is currently available and able to run on biomass fuels with greater availability than petroleum.

EXAMPLES

Example 1

Conjugates and Self-Assembly

This example illustrates self-assembly of three-dimensional solid-state nanostructures containing approximately 33% by weight globular protein is demonstrated using a globular protein-polymer diblock copolymer, providing a route to direct nanopatterning of proteins for use in bioelectronic and biocatalytic materials. A mutant red fluorescent protein, mCherryS131C, was prepared by incorporation of a unique cysteine residue and site-specifically conjugated to end-functionalized poly(N-isopropylacrylamide) through thiol-maleimide coupling to form a well-defined model protein-polymer block copolymer. The block copolymer was self-assembled into bulk nanostructures by solvent evaporation from concentrated solutions. Small-angle X-ray scattering and transmission electron microscopy illustrated the formation of highly disordered lamellae or hexagonally perforated lamellae depending upon the selectivity of the solvent during evaporation. Solvent annealing of bulk samples resulted in a transition towards lamellar nanostructures with mCherry packed in a bilayer configuration and a large improvement in long range ordering. Wide-angle X-ray scattering indicated that mCherry did not crystallize within the block copolymer nanodomains and that the $\beta$-sheet spacing was not affected by self-assembly. Circular dichroism showed no change in protein secondary structure after self-assembly, while UV-vis spectroscopy indicated approximately 35% of the chromophore remained optically active.

Results and Discussion:

Globular Protein-Polymer Diblock Copolymer Synthesis.

A model globular protein-polymer conjugate with a single well-defined bioconjugation site was synthesized using the red fluorescent protein mCherry and the thermoresponsive synthetic polymer PNIPAM. The protein mCherry was selected because the native sequence lacked cysteine residues, the high yield expression and purification of folded protein are well-established, and the fluorescent nature provided a simple and robust spectrophotometric method for conjugate characterization. The protein mCherry was mutated to introduce a unique thiol conjugation site into its sequence by replacing serine with cysteine at residue 131, yielding the mutant mCherryS131C. The mutation is located in a loop region on the end of the $\beta$-barrel structure opposite both the N and C termini, as illustrated in FIG. 1. A 6x His-tagged variant of this protein was expressed in *Escherichia coli* (*E. coli*) and then purified using metal affinity chromatography under native reducing conditions to preserve the delicate chromophore bond and prevent thiol inactivation. The yield of purified protein, determined spectrophotometrically at 586 nm based on the known extinction coefficient of mCherry, was 121 mg/L culture.

Figure 2:
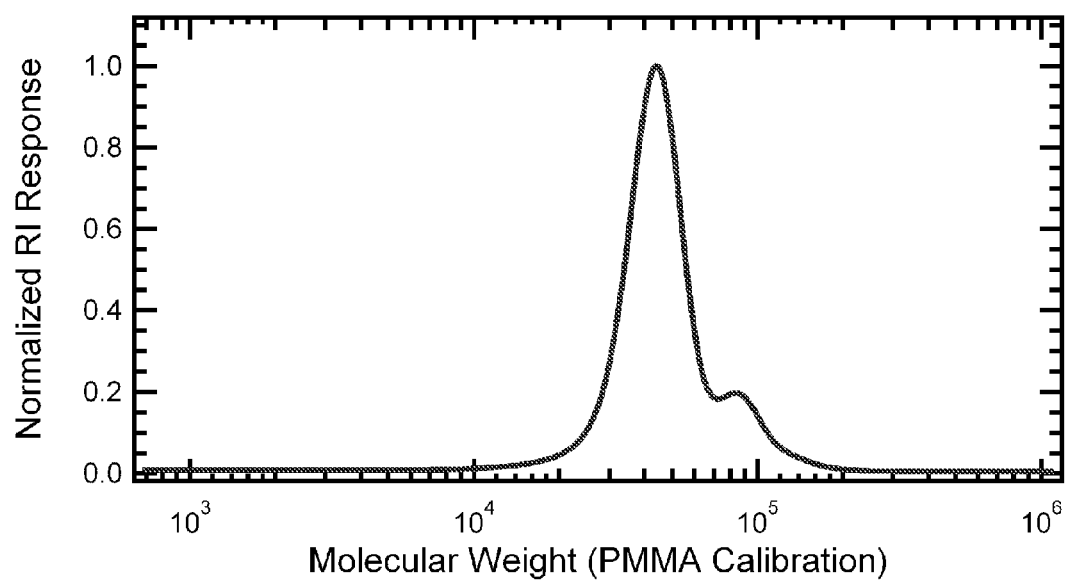
FIG. 2 shows typical results of a normalized gel permeation chromatography trace of deprotected poly(N-isopropylacrylamide) product with a poly(methyl methacrylate)-equivalent molecular weight of 51.3 kg/mol and a polydispersity of 1.24

The diblock copolymer was synthesized by conjugating mCherryS131C to maleimide-functionalized PNIPAM. A reversible addition-fragmentation chain transfer (RAFT) agent containing a protected maleimide group was used to synthesize low polydispersity PNIPAM (FIG. 1). After polymerization, the maleimide group was thermally deprotected to yield maleimide end-functionalized PNIPAM with a molar mass of 51.3 kg/mol and a polydispersity of 1.24. Gel permeation chromatography (GPC) analysis is shown in FIG. 2. The polydispersity in these samples originates in part from a small shoulder at twice the peak molecular weight in the GPC trace that represents 8% of the total polymer mass. This minor high molecular weight fraction is believed to originate from a slight reactivity of the double bond in the protected maleimide group on the RAFT agent during polymerization to conversions greater than 50%. When an identical RAFT agent is used without the protected maleimide functionality, no coupling is observed.

Figure 3:
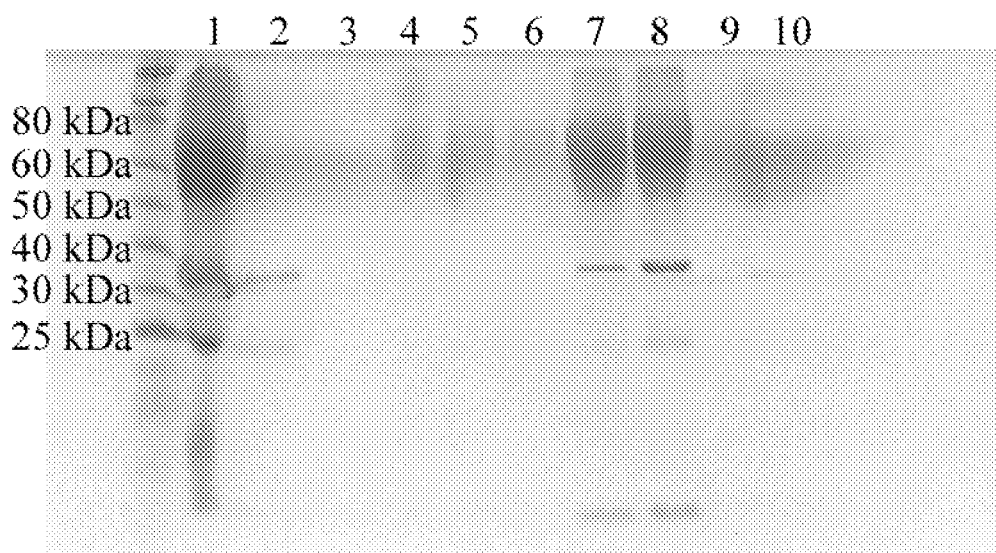
FIG. 3 shows typical results of a denaturing SDS-PAGE gel showing purification of an mCherryS131C-PNIPAM conjugate. The crude reaction mixture (lane 1) was purified by repeated precipitation of the conjugate using ammonium sulfate to remove unconjugated mCherryS131C. The discarded supernatants (lanes 2 and 3) contained most of the unconjugated mCherry. Next, metal affinity chromatography was used to remove excess PNIPAM. Minimal conjugate is lost from the column flow through (lane 4) and the two wash steps (lanes 5 and 6). The conjugate is then eluted in four fractions (lanes 7-10).
Figure 9:
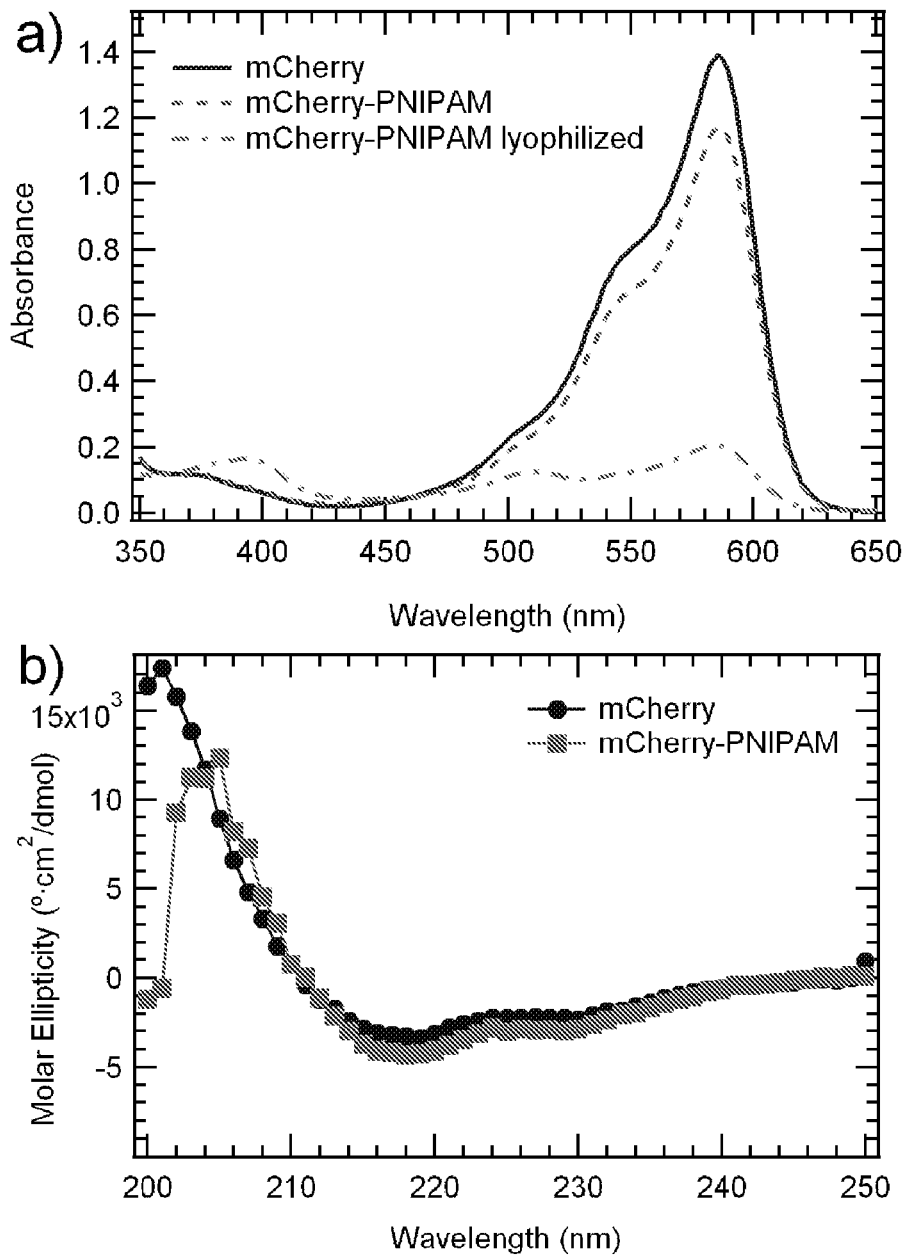
FIG. 9 shows typical results of a) UV-vis spectra in solution indicating minimal change in the mCherryS131C chromophore after conjugation to PNIPAM. The spectrum of the mutant mCherryS131C is quantitatively identical to that of the parent protein. This is in contrast to the dramatic change observed after lyophilization. b) Circular dichroism spectra of mCherryS131C and its conjugate with PNIPAM in solution indicate the protein folding is not disrupted by conjugation.

Bioconjugation was then performed at room temperature in 20 mM Tris buffer (pH 8) using a eight-fold excess of PNIPAM. SDS-PAGE of the crude conjugation product and purified fractions is shown in FIG. 3. The band at approximately 70,000 g/mol corresponds to the mCherry-PNIPAM conjugate with a PNIPAM volume fraction of 0.66 and a weight fraction of 0.66. The band at 28,000 g/mol corresponds to unconjugated mCherry, while the bands at 19,000 g/mol and 9,000 g/mol correspond to the partial hydrolysis of the mCherry chromophore acylimine bond during SDS-PAGE analysis. Lane analysis of the crude reaction mixture revealed a conversion of approximately 78%, comparable to previously reported conversions for thiol-maleimide couplings to globular proteins. Although the eight-fold excess of PNIPAM used gave maximum conversion of the mCherryS131C, decreasing to a five-fold excess still yielded approximately 70% conversion. After conjugation, unreacted mCherry was removed using ammonium sulfate precipitation; SDS-PAGE showed that after the first precipitation no additional unreacted mCherry is removed. Unconjugated PNIPAM was subsequently removed by metal affinity chromatography; washing with 7 column volumes of buffer was used to ensure complete removal of the free PNIPAM. Analysis of the second elution lane (lane 8) suggests that the conjugate is >90% pure, while the third elution lane (lane 9) demonstrates that at lower protein concentrations only the conjugate band is visible. The purified conjugate was obtained in a final yield of 30%. Circular dichroism and UV-vis spectroscopy (FIG. 9) confirmed that the protein structure and optical properties in the purified mCherry-PNIPAM diblock remained unchanged from that of the mCherryS131C in solution. Cloud point measurements (Table 1) show that the thermal transition of the conjugate increases by ~5° C. relative to that of the homopolymer due to addition of the large hydrophilic protein.

Table 1: Cloud points of mCherryS131C-PNIPAM and the corresponding homopolymer. Solutions were prepared at 1.26 mg/mL PNIPAM and the absorbance at 700 nm was monitored as the temperature was ramped from 20 to 50° C. at 0.1° C./min. A PNIPAM molecular weight of 35.5 kg/mol was used for both conjugate and homopolymer measurements. Increasing PNIPAM molecular weight would decrease the transition temperatures.

| Sample | Thermal Transition (° C.) |
| --- | --- |
| PNIPAM | 33.5 |
| mCherryS131C-PNIPAM | 38.6 |

Nanostructure Formation.

Figure 4:
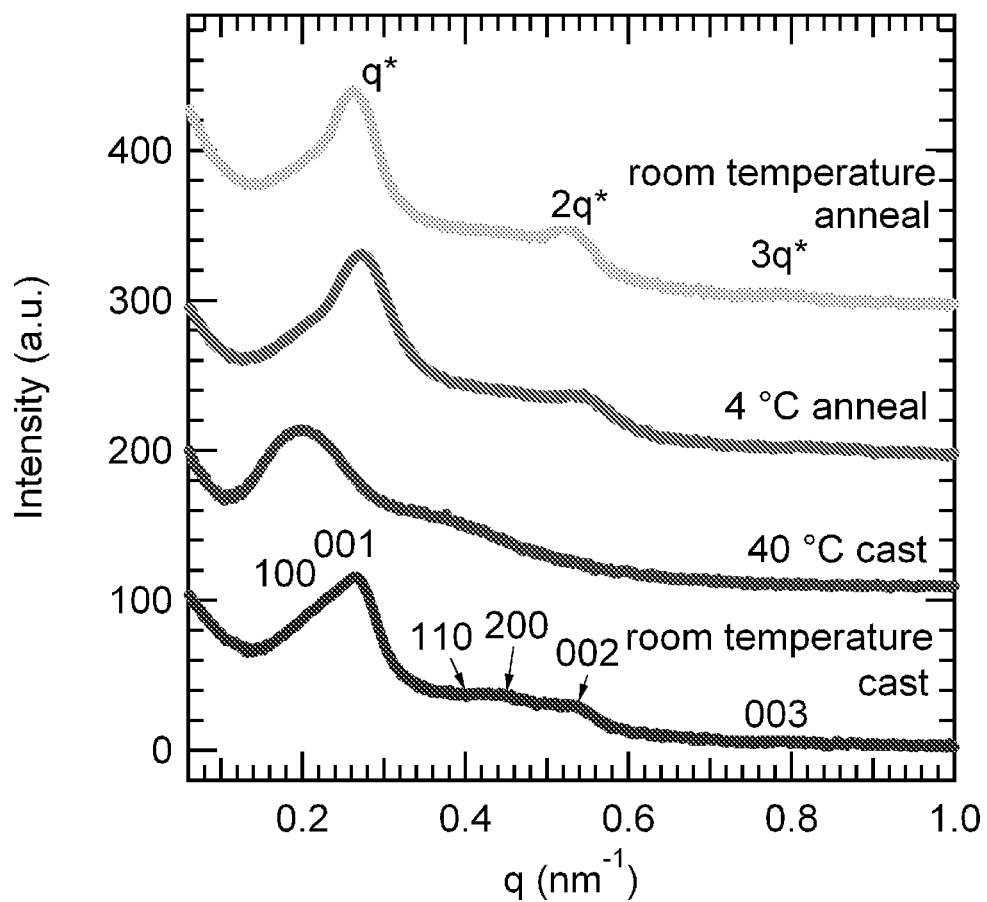
FIG. 4 shows typical results of small-angle x-ray scattering (SAXS) data of as-cast and solvent annealed mCherry-PNIPAM block copolymers. Samples were cast from both protein-selective (40° C. water) and nonselective (room temperature water) solvents. The materials form long-range ordered nanostructures with weak order. After solvent annealing in water, the samples transition to lamellar nanostructures with improved long-range order. Traces have been offset for clarity.
Figure 5:
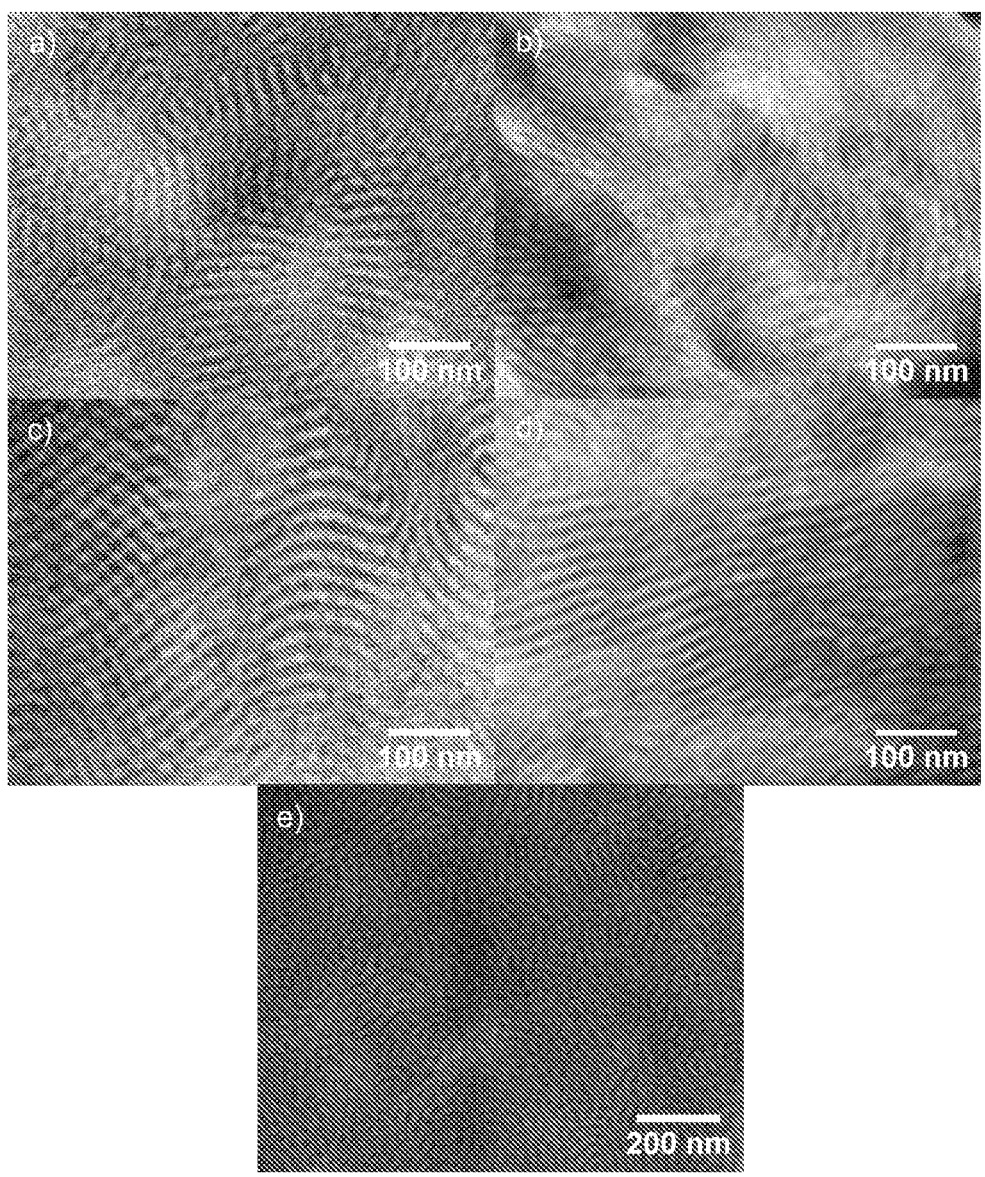
FIG. 5 shows typical TEM images of mCherry-PNIPAM block copolymers demonstrating the formation of lamellae and hexagonally perforated lamellae in bulk samples cast at 40° C. (a) or room temperature (b), and samples cast at room temperature followed by solvent annealing in water at 4° C. (c) or room temperature (d). Panel e shows the 40° C. cast sample at a lower magnification.
Figure 6:
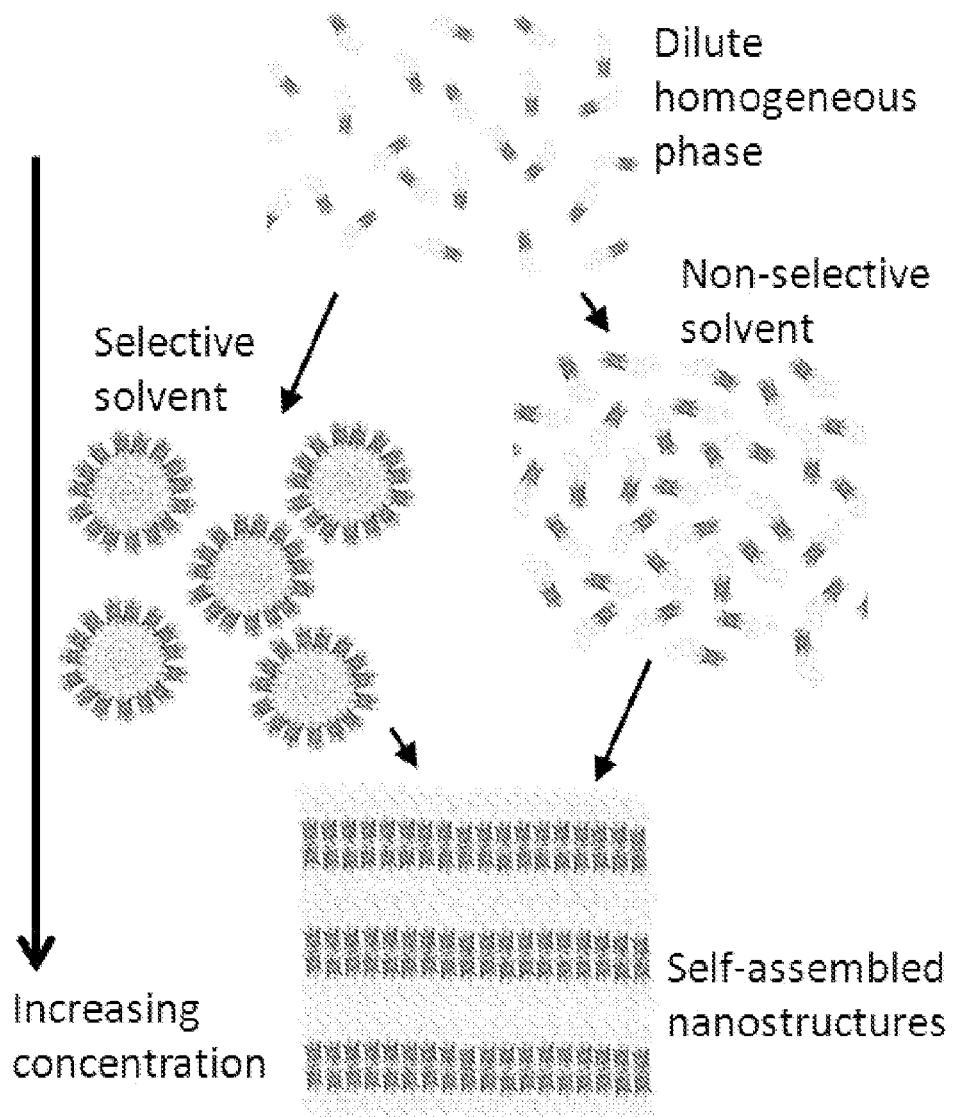
FIG. 6 illustrates a schematic of two possible pathways towards self-assembly of mCherry-PNIPAM block copolymers. Room temperature water provides a nonselective solvent, whereas 40° C. water is a protein-selective solvent. Self-assembly is induced by increasing the block copolymer concentration through solvent evaporation.

Self-assembly of mCherry-PNIPAM diblock copolymers was accomplished through evaporation of water from diblock copolymer solutions to form nanostructured bulk plastics. The formation of nanostructures strongly depends on the processing conditions used to prepare the material, as demonstrated by small-angle X-ray scattering (SAXS), shown in FIG. 4, and transmission electron microscopy (TEM) images, shown in FIG. 5. In the TEM images, the mCherry areas appear dark due to staining with ruthenium tetroxide which reacts with alcohols, amines and aromatics present on the protein surface. Two processing pathways were explored for water evaporation: a protein-selective solvent (40° C. water, above the lower critical solution temperature (LCST) of the PNIPAM homopolymer) and a nonselective solvent (room temperature water), as illustrated in FIG. 6.

Both as-cast samples contain multiple peaks in their SAXS patterns, indicating the formation of long-range ordered nanostructures. The nanostructures formed from a nonselective solvent exhibit two sets of peaks, a relatively intense set that can be indexed to a lamellar structure and a weaker set that may be indexed to a hexagonal lattice. The primary peak is asymmetric, composed of a 001 peak and a low q 100 shoulder. The first higher order reflections may be indexed to 110, 200, 002, and 003, corresponding to peaks from both a hexagonal and a lamellar lattice. These peak observations are consistent with a hexagonally packed lamellar (HPL) morphology with a lamellar domain spacing of 23.4 nm and a hexagonal domain spacing of 26.5 nm. The 002 and 003 scattering peaks, corresponding to the lamellar spacing, are much more intense than the 110 and 200 scattering peaks corresponding to the hexagonal perforations, as is typical for HPL structures. TEM images of the sample provide evidence for HPL formation and are consistent with previously reported images of HPL from coil-coil diblock copolymers. The micrograph in FIG. 5b shows areas of lamellar structure with perforations parallel to the lamellar normal as well as regions of the sample that have a hexagonally packed structure. These two structures are consistent with different orientations of the HPL unit cell in the sample. The formation of an HPL morphology at a PNIPAM volume fraction of 0.66 is similar to that found in coil-coil block copolymer systems where HPL morphologies are typically seen as non-equilibrium structures in a narrow window between lamellae and cylinders. Even though the protein is the minority block in these copolymers, the protein domains perforate the coil regions. This suggests that the protein remains more highly hydrated than the PNIPAM during sample casting, increasing its effective volume fraction.

The assembled nanostructures from a protein-selective solvent show poorer ordering than those obtained from a nonselective solvent. The protein-selective solvent results in a relatively broad primary peak with a broad second order shoulder centered around a q value twice that of the primary peak. While the observed peak positions are consistent with the formation of lamellar nanostructures, the broad peaks indicate that the order in this sample is poorer than that in the sample cast from nonselective solvent. The TEM images in FIG. 5a,e show the structurally heterogeneous nature of this sample containing small lamellar regions with hexagonally packed areas interspersed. These images show that the sample is composed of undulating lamellae along accompanied by regions of hexagonal structures with PNIPAM centers similar to the structure of the sample cast from a nonselective solvent. These structures may be the result of micelles which merged to form sheets. A lower magnification image (FIG. 5e) reveals that these lamellar regions are interspersed with spherical protein aggregates, and that these domains are inverted from the observed HPL morphologies. Because this sample was prepared from a state where the protein and polymer are segregated due to immiscibility of the solvent and polymer, it is likely that kinetic barriers to nanoscale structural rearrangement during solvent evaporation result in the structural heterogeneity and a relatively low degree of order.

In comparison to the sample cast in the nonselective solvent, the sample cast from protein-selective solvent has a larger domain spacing of 32.1 nm, as measured by SAXS. However, TEM images suggest that the domain sizes for the more highly ordered (FIG. 5a) and more disordered (FIG. 5e) regions of the protein-selective solvent cast sample differ significantly. Fourier transforms of the images of well-ordered lamellar regions and the disordered regions indicate that the disordered regions are 40% larger than the lamellar regions. This increased domain spacing observed at larger length scales is consistent with the 37% larger domain spacing observed by SAXS of the protein-selective solvent compared to the lamellar sample from a nonselective solvent. The observed difference in domain spacing for disordered and lamellar regions of the protein-selective solvent condition suggests that the equilibrium lamellar spacing would be quite similar for both casting conditions; however, the processing-dependent effects that lead to the high degree of structural heterogeneity and kinetic trapping of nonequilibrium structures for the protein-selective solvent result in a large increase in the average domain spacing.

Solvent annealing of samples cast from the nonselective solvent condition was used to probe whether the HPL structure was at equilibrium. Annealed samples show enhanced ordering of the nanodomains with a clear lamellar symmetry and a domain spacing corresponding to the lamellar spacing observed in the as-cast sample, suggesting that the lamellar phase is closer to thermodynamic equilibrium for this sample. After annealing in water at either 4° C. or room temperature for 8 hours, the primary peak shifted to slightly lower q* than in the as-cast sample, all reflections in the SAXS pattern became sharper, and the two higher order reflections now occur at 2q* and 3q*, consistent with the formation of lamellae. TEM confirms the formation of lamellar nanostructures in the room temperature annealed sample while some hexagonally perforated lamellae are still present in the sample annealed at 4° C. Both annealed samples show clear layered structures and larger grain sizes than the as-cast sample. In addition, dislocations typical of lamellar block copolymers may be observed in the annealed samples. The improvements in translational and orientational order are consistent with the sharpening of scattering peaks and the observation of the third order reflection. In addition, the lamellae are relatively straight as compared to the typical fingerprint patterns observed in coil-coil diblocks. The nanodomain persistence length appears to be longer than that of coil-coil block copolymer domains, but shorter than that of typical rod-coil block copolymer domains. This observation is likely due to the small, yet well-defined rigid shape of the mCherry protein which may introduce an enhanced bending rigidity within the nanodomains relative to that of a coil-coil diblock copolymer.

Although both solvent annealed samples show an evolution towards lamellar structures, the disappearance of the low q shoulder on the primary peak and the appearance of the third order peak are both more pronounced in the sample annealed at room temperature. In addition, the domain spacing of the sample annealed at room temperature (24.0 nm) is larger than the domain spacing of the sample annealed at 4° C. (23.1 nm). While both annealing conditions were chosen to occur in the nonselective solvent regime, both the chemical potential of water and the water-PNIPAM interactions are strongly temperature dependent. The PNIPAM block is anticipated to have a more favorable interaction with water at lower temperature, but the chemical potential of water vapor during solvent annealing decreases as a function of temperature. Both the slightly larger domain spacing and the increased degree of ordering observed in the room temperature annealed sample suggest that the increased chemical potential of water at higher temperature dominates the annealing behavior, resulting in increased swelling of the lamellar nanostructures and accounting for the increase in domain spacing. In addition, both higher temperature and higher water content will increase the mobility of the polymer, consistent with the observation of more intense higher order peaks and a stronger depletion of the hexagonally perforated lamellar phase in the sample annealed at room temperature.

Using scaling relationships for domain spacing as a function of molecular weight, the proteins may be inferred to pack in a bilayer structure within the lamellae. Based on the crystallographic structure of mCherry, the protein has a length of approximately 4.2 nm in the folded state. Because the folded proteins are rigid, the same scaling analysis for domain spacing in rod-coil diblock copolymers is expected to apply. For the mCherry-PNIPAM diblocks, this would yield an expected domain spacing of ~12.4 nm in the monolayer configuration. Because this value is approximately half that of the experimentally observed domain spacing, it is most likely that the mCherry is packed in a bilayer configuration within the lamellar nanodomains.

Protein Assembly within the Nanodomain Structure.

Figure 7:
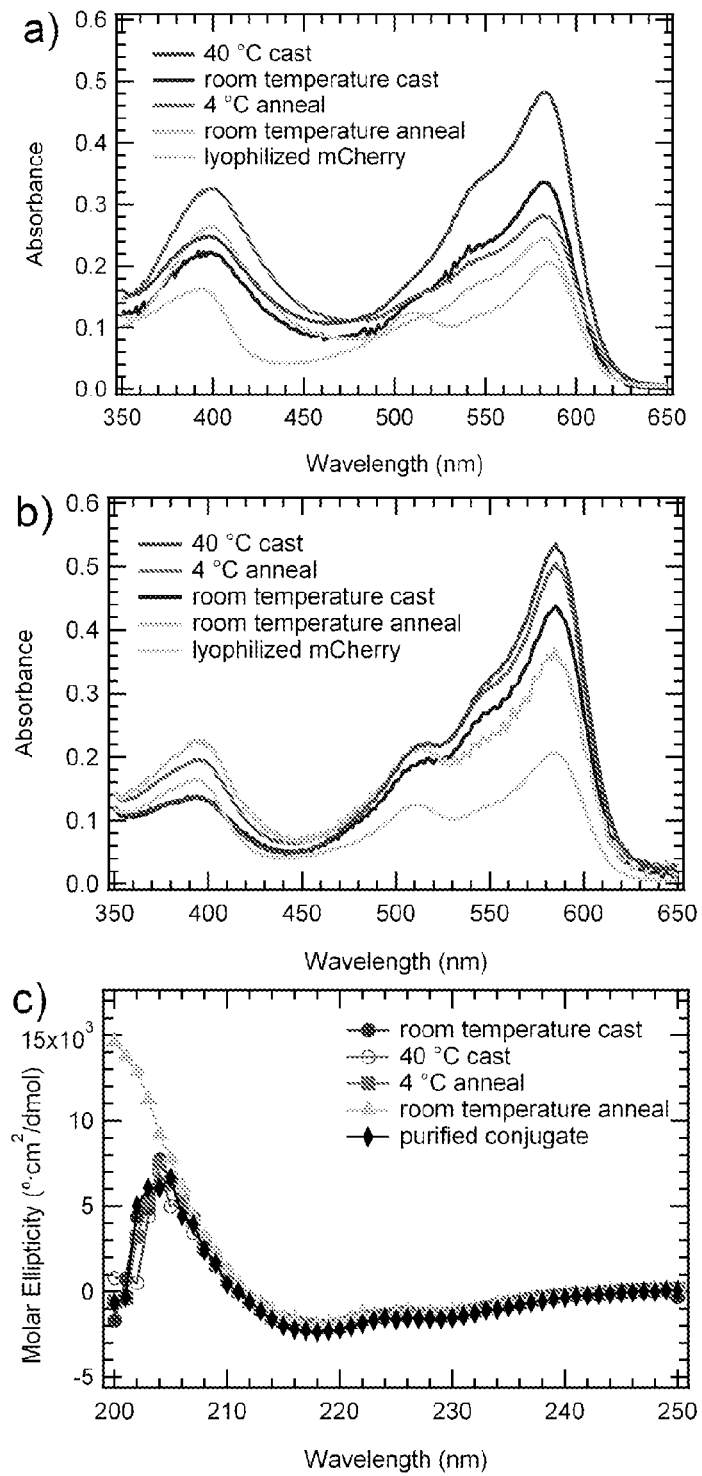
FIG. 7 shows typical results of a) Solid state UV-vis spectra of mCherry-PNIPAM conjugate normalized by $A_{280}$; b) Rehydrated solid state UV-vis spectra of mCherry-PNIPAM conjugate normalized by $A_{280}$ showing retention of the characteristic absorbance peak shape of mCherry at 586 nm; and c) Rehydrated solid-state circular dichroism spectra of conjugate showing protein fold is not disturbed by self-assembly.

To enable the fabrication of nanostructured protein-based materials, the protein in these self-assembled block copolymers must remain properly folded and functional. The functionality of mCherry in solid-state mCherry-PNIPAM materials was quantified using both UV-vis spectroscopy and circular dichroism, demonstrating that the self-assembly process preserves a large fraction of the protein structure and optical activity. UV-vis spectra were measured for solid-state samples (FIG. 7a) and for rehydrated diblock copolymers (FIG. 7b). In the solid state, the peak absorption of the mCherry chromophore at 586 nm remains unchanged, but the shoulder near 550 nm increases in intensity relative to the peak, suggesting a change in absorbance in the solid state. This change is reversed when the materials are rehydrated. The diminishing of the absorbance peak at 586 nm and the enhancement of the shoulder at 510 nm and the peak at 390 nm in both solid-state and rehydrated samples indicates that the chromophore for some fraction of the material has been disrupted. A peak at 386 nm has been observed previously in similar red fluorescent proteins and has been attributed to the addition of water across the acylimine chromophore bond.

Figure 10:
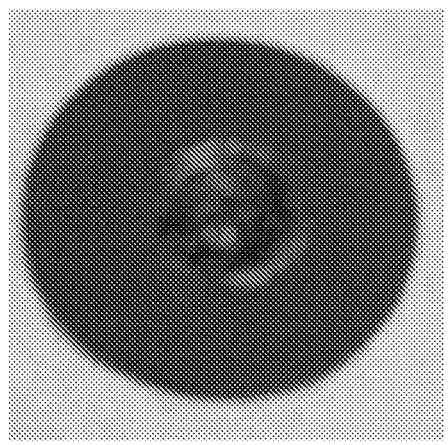
FIG. 10 shows an exemplary photograph of mCherry-PNIPAM block copolymer sample cast at room temperature and used for SAXS data acquisition showing the deep red color of mCherry. The sample is 7 mm in diameter and approximately 0.5 mm in height.

Because quantum overlap in the solid state may influence the spectrum, a quantitative measure of the functionality of the materials was performed by measuring their absorbance spectrum upon rehydration in milli-Q water. Compared to the UV-vis data for as-synthesized protein-polymer conjugates in solution (FIG. 9), the rehydrated samples show a decrease in the ratio of $A_{586}:A_{280}$ from approximately 1.3 to 0.5. This indicates that for all four samples 30-40% of the protein remains active when compared to the conjugate in solution. Consistent with preservation of approximately 35% of the protein's optical activity, the bulk material appears to have a deep red color (FIG. 10). Rehydration also results in a decrease in the peak absorbance at 390 nm to some level intermediate between the as-synthesized and the solid-state materials. This suggests the presence of three types of mCherry chromophore in the solid state: active, irreversibly inactive, and spectrally shifted. The active fraction is responsible for the major absorbance peak at 586 nm. The peak at 390 nm increases in the solid-state material then decreases upon rehydration, suggesting that a significant contribution to this peak comes from the spectrally shifted material. The shoulder at 510 nm also increases upon rehydration, suggesting that there is a fraction of irreversibly inactivated chromophore that absorbs at this wavelength only after rehydration. Some of the irreversibly inactivated chromophore may also have no absorption within the visible region.

In the dehydrated samples, it is observed that the extent of processing correlates with a loss of optical function in the protein. The relatively rapid casting process at 40° C. tends to promote a higher fraction of active chromophore compared to other samples by about 10%. Because the sample cast at 40° C. was never exposed to high vacuum, it is likely that it contains residual water that enhances the stability of the protein through hydrogen bonding. The room temperature cast sample has the next highest fraction of active chromophore, followed by the two solvent annealed samples which show a further decrease in absorbance at 586 nm and an increase in absorbance at 390 nm. By comparison, a control sample of lyophilized mCherry retains less than 15% of its optical activity at 586 nm, worse than any of the self-assembled materials. Upon rehydration, the relative order of peak intensities in the solid-state and rehydrated spectra changes. While all samples show an increase in the absorbance at 586 nm after rehydration, the sample solvent annealed at 4° C. shows the largest increase, indicating that it contains the largest fraction of reversibly inactive material.

Circular dichroism spectra of the rehydrated conjugates show very little change from the conjugate before self-assembly. This indicates that the majority of the protein retains identical secondary structure as the native protein, even after having been dehydrated and rehydrated. Quantitative analysis of the spectra showed that the mCherry alone was composed of 50% β-sheet, as compared to a theoretically predicted 57% β-sheet content from the crystal structure. The discrepancy between the measurement and prediction is accounted for by the presence of the 6× His tag region in the experimental protein but not in the crystal structure. The mCherry-PNIPAM block copolymer in solution after purification was 43% β-sheet, and the rehydrated samples contained 41-48% β-sheet, indicating no loss of secondary structure upon PNIPAM conjugation within the resolution of the measurement. Taken together, the circular dichroism and UV-vis data illustrate that it is possible to maintain a substantial degree of globular protein fold and function in a solid-state self-assembled block copolymer. Because the fold is maintained to a much higher degree than the chromophore activity, it is likely that the activity of the sensitive chromophore is lost during self-assembly without large changes in the protein structure.

Figure 8:
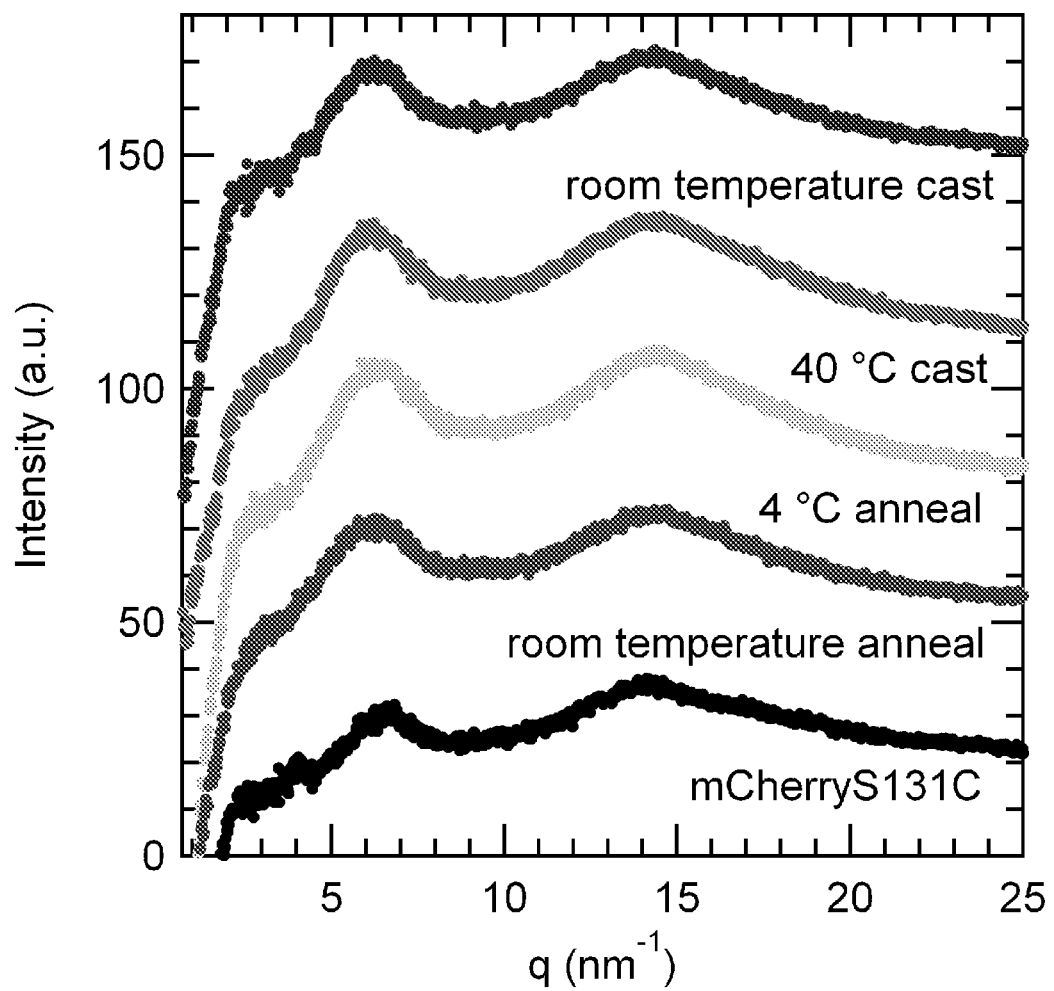
FIG. 8 shows typical wide-angle x-ray scattering data of as-cast and solvent annealed mCherry-PNIPAM block copolymers shows scattering due to the inter-sheet and inter-strand spacing of β-strands. The spacing of the β strands of mCherry is not altered in conjugate materials.

The packing and crystallinity of the mCherry within the block copolymer nanodomains was investigated using wide-angle X-ray scattering (WAXS), shown in FIG. 8. The scattering patterns of self-assembled conjugates contain the same two peaks as a bulk sample composed of solid mCherry prepared by evaporation from solution. This demonstrates that the WAXS peaks seen for the block copolymer samples are a result of the mCherry structure and not affected by the PNIPAM. No peaks are present corresponding to the mCherry crystal structure, indicating that the mCherry is in an amorphous state. This is consistent with both kinetic limitations to crystallization during the self-assembly process, which occurs on a timescale of ~2 hrs, and with UV-vis results that suggest a portion of the protein may be structurally perturbed in the solid state and therefore unable to crystallize within the mCherry unit cell.

WAXS data for the mCherry protein indicate that the material retains a predominantly β-barrel structure in the solid state. All of the block copolymers contain two peaks, one at approximately 6.23 $nm^{-1}$ and the other at 14.32 $nm^{-1}$ corresponding to 1.0 and 0.45 nm, respectively, in real space. The larger domain spacing peak is attributed to either inter-sheet spacing or inter-helix spacing for proteins containing β-sheets or α-helices, respectively. The smaller domain spacing peak arises from inter-strand hydrogen bonding in β-sheet proteins, or backbone hydrogen bonding in α-helices. Given that circular dichroism and the known crystal structure of mCherry suggest a predominantly β-sheet secondary structure, these peaks are inferred to result from inter-sheet spacing and inter-strand hydrogen bonding between β-strands. Because the q values of these peaks do not change between samples, it is concluded that the inter-sheet and inter-strand spacing is not changed significantly by the processing method used to induce self-assembly. The block copolymer samples all show similar intensities for both peaks with the ratio of the 6.23 $nm^{-1}$ to the 14.32 $nm^{-1}$ peak equal to approximately 0.98. In contrast, mCherry shows a higher intensity for the second peak with a ratio of 0.84. An increase in this ratio has previously been correlated with a decrease in β-sheet content, suggesting that the β-sheet content is slightly lower in the self-assembled block copolymers than in the bulk mCherry. This result is consistent with the minor decrease in β-sheet content upon bioconjugation observed by CD.

Conclusions:

Protein-polymer diblock copolymers composed of mCherryS131C and PNIPAM were synthesized and self-assembled into nanostructured materials, demonstrating an attractive route towards high density three-dimensional protein nanopatterning with precise control over protein orientation and placement. Self-assembly was induced by solvent evaporation, and the selectivity of the solvent during the evaporation process was shown to have a large effect on the nanostructure formed, resulting in a heterogeneous nanodomain structure for a protein-selective solvent and a hexagonally perforated lamellar phase for a nonselective solvent. Subsequent solvent annealing resulted in an evolution towards well-ordered lamellar structures, suggesting that this lamellar structure may be closer to thermodynamic equilibrium. After annealing at room temperature, SAXS indicated a domain spacing for the material of 24.0 nm, suggesting that the mCherry packs in bilayers within the lamellae. The mCherry structure within the lamellar domains was largely amorphous, with the only observed WAXS peaks assigned to inter-sheet and inter-strand spacing of β-strands. While circular dichroism indicated no irreversible change in protein secondary structure after self-assembly, UV-vis spectroscopy showed that one third of the protein chromophores remained active in the solid-state material.

Methods:

Synthesis of 2-Ethylsulfanylthiocarbonylsulfanyl-2-Methyl Propionic Acid (EMP).

This procedure was adapted from the work of You and Oupický. First, ethanethiol (7.21 mL, 0.1 mol), acetone (73 mL), and tricaprylylmethylammonium chloride (1.0 g, 2.5 mmol) were combined and the mixture was cooled on ice under nitrogen. Next, 9 mL of 50% (w/v) of sodium hydroxide was added dropwise. After an additional 20 minutes, carbon disulfide (6.03 mL, 0.1 mol) and acetone (12.6 mL) were combined and added dropwise. Chloroform (12 mL, 0.15 mol) was added, followed by the addition of 80 mL of 50% (w/v) sodium hydroxide over 10 minutes. The yellow-orange mixture was stirred overnight. Water (200 mL) was added, followed by concentrated hydrochloric acid (80 mL) to drop the pH below 1. The mixture was extracted three times into diethyl ether and concentrated to a dark red oil. Crude product was purified via silica gel chromatography (1:1 hexanes:ether) and then distilled to yield 11.0 g of a bright orange, viscous liquid (49% yield). 1H NMR ($CDCl_3$, δ): 1.33 (t, 3H, —$CH_2CH_3$), 1.72 (s, 6H, —$C(CH_3)_2COOH$), 3.30 (q, 2H, —$CH_2CH_3$).

Synthesis of exo-3a,4,7,7a-tetrahydro-2-(3-hydroxypropyl)-4,7-epoxy-14-isoindole-1,3(2H)-dione (1).

Following the work of Neubert and Snider, 3-amino-1-propanol (4.08 g, 54.2 mmol) was added dropwise to a solution of exo-3,6-epoxy-1,2,3,6-tetrahydrophthalic anhydride (9.0 g, 54.2 mmol) in 500 mL methanol. The reaction was stirred at 56° C. for 3 days, after which the solvent was removed by rotary evaporation to give a clear yellow oil. 100 mL dichloromethane was added and washed three times with 100 mL brine. The organic fraction was dried over sodium sulfate and the solvent removed under reduced pressure to give 2.71 g of a white solid (22% yield). 1H NMR (CDCl$_3$, δ): 1.75 (tt, 2H, —CH$_2$(CH$_2$)CH$_2$—), 2.88 (s, 2H, —NC(O)CH—), 3.52 (t, 2H, —NCH$_2$—), 3.65 (t, 2H, —CH$_2$O—), 5.27 (s, 2H, —CH(O)—), 6.52 (s, 2H, —CHCH—).

Synthesis of RAFT Agent.

Functional RAFT agent was prepared by carbodiimide coupling. EMP (1.88 g, 8.40 mmol), 1 (1.50 g, 6.72 mmol), 4-dimethylaminopyridine (103.8 mg, 0.84 mmol), and N,N'-dicyclohexylcarbodiimide (3.46 g, 16.8 mmol) were combined in 58 mL dry tetrahydrofuran and stirred under nitrogen at room temperature overnight. The reaction mixture was filtered and concentrated, and the product was purified by silica gel chromatography (1:1 hexanes:ethyl acetate) to yield 1.23 g of a bright yellow solid (34% yield). 1H NMR (CDCl$_3$, δ): 1.29 (t, 3H, —S—CH$_2$CH$_3$), 1.69 (s, 6H, —C(CH$_3$)$_2$—), 1.85-2.00 (tt, 2H, —CH$_2$(CH$_2$)CH$_2$—), 2.83 (s, 2H, —NC(O)CH—), 3.26 (q, 2H, —CH$_2$CH$_3$), 3.55 (t, 2H, —NCH$_2$—), 4.05 (t, 2H, —CH$_2$O—), 5.24 (s, 2H, —CH(O)—), 6.49 (s, 2H, —CHCH—).

Polymerization.

The RAFT agent and azobisisobutyronitrile (AIBN) (recrystallized twice from methanol) were added to a 2.0 M solution of NIPAM (sublimated) in acetonitrile in the ratio 600:1:0.2 (monomer:RAFT agent:initiator). The solution was degassed by three freeze-pump-thaw cycles. The polymerization was carried out in a sealed flask at 65° C. and terminated after 75 minutes by removal of heat and exposure to oxygen. The polymer was then precipitated in cold diethyl ether and dried under vacuum. The maleimide was deprotected by heating to 120° C. under vacuum for 2 hours. The molecular weight and polydispersity were determined by gel permeation chromatography using a Waters Breeze 1525 HPLC system with a series 2414 refractive index detector, calibrated with poly(methyl methacrylate) standards, and N,N-dimethylformamide with 0.01 M LiBr as the mobile phase.

Cloning and Protein Expression.

The gene for mCherry, optimized for prokaryotic codon usage, was subcloned into the pQE9 vector (Qiagen) which encodes for an N-terminal His tag. Site directed mutagenesis was used to create the mutant mCherryS131C by replacing a serine with a cysteine at residue 131, located in a loop region on the end of the β-barrel opposite the N and C termini. The protein was expressed in the E. coli strain SG13009 containing the pREP4 repressor plasmid, grown in Terrific Broth at 37° C., and induced with 1 mM Isopropyl β-D-1-thiogalactopyranoside (IPTG) at OD$_{600}$=1. The cells were cultured for 4.5 hours after induction and were then harvested. The cell were resuspended in lysis buffer (50 mM NaH$_2$PO$_4$, 300 mM sodium chloride, 10 mM imidazole, 10 mM β-mercaptoethanol (BME), pH 8.0), incubated with 1 mg/mL lysozyme at 4° C. for 30 minutes and sonicated. The lysate was clarified, and the protein was purified using Ni-NTA metal affinity chromatography. Throughout the purification, 10 mM BME was used in all buffers. Elution fractions containing purified protein were dialyzed into 20 mM Tris buffer, pH=8. The yield in the elution fractions was determined spectrophotometrically using the absorbance peak at 586 nm (extinction coefficient of 72,000 M$^{-1}$cm$^{-1}$).

Figure 11:
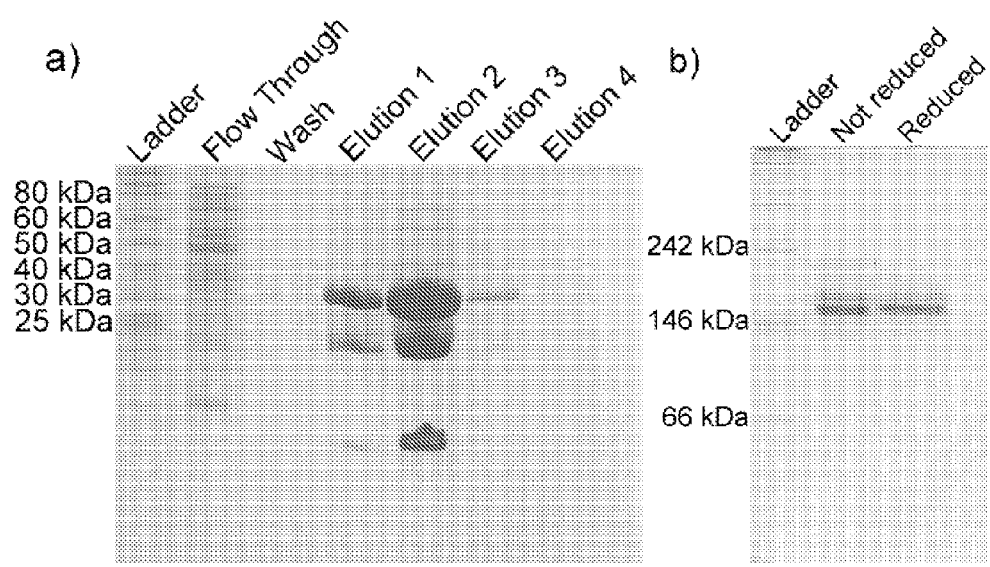
FIG. 11 shows typical results of a) SDS PAGE denaturing gel showing mCherryS131C purity. The two smaller molecular weight segments are the result of the chromophore acylimine bond breaking during protein boiling. b) Native gel showing that mCherry remains intact throughout the purification process. A higher molecular weight band shows the presence of dimers formed through disulfide linkages; the dimers are more prevalent under non-reducing conditions. Reduced mCherry was obtained by adding an equimolar amount of β-mercaptoethanol and allowing the reaction to occur at room temperature for one hour.

The purity of the protein was confirmed by denaturing gel electrophoresis (SDS-PAGE), native state gel electrophoresis, and matrix assisted laser desorption ionization mass spectrometry (MALDI-MS). SDS-PAGE (FIG. 11) shows three bands near 28 kg/mol, 19 kg/mol and 9 kg/mol due to partial cleavage of the protein during sample boiling before loading the gel. The highest molecular weight band corresponds to the expected molar mass of the whole mCherry molecule, and the sum of the molar masses of the two lower mass bands also corresponds to the mass of the whole protein, consistent with hydrolysis of the sensitive acylimine bond within the mCherry chromophore. The native gel (FIG. 11), run at a high protein concentration, shows only a single prominent protein band corresponding to the mCherry and a higher molecular weight band corresponding to dimerization through the formation of a disulfide bond. Consistent with previously reported expressions of mCherry, it is noted that the lower molar mass fragments are not observed by SDS-PAGE in more dilute samples. The observation of a single dominant band in the native gel indicates that cleavage occurs only during SDS-PAGE sample preparation. The purity of the protein was further confirmed by MALDI-TOF mass spectrometry; the measured molar mass of the protein was 28,201 g/mol compared to the expected mass of 28,134.48 g/mol. No peak was observed for the higher molar mass hydrolysis product (18,896 g/mol calculated molar mass), although a small peak was observed for the low molecular weight fragment (9,256 g/mol calculated molar mass), consistent with the preferential observation of low molecular weight species by MALDI.

Bioconjugation.

The coupling reaction between mCherryS131C and maleimide end-functionalized PNIPAM was performed in 20 mM Tris buffer, pH 8.0. Tris(2-carboxyethyl)phosphine (TCEP) (0.0185 g, 0.0646 mmol) was added to the mCherryS131C solution (0.173 g, 0.00646 mmol, 1.8 mg/mL) one hour prior to PNIPAM addition to reduce all thiol groups. Maleimide functionalized PNIPAM (2.61201 g, 0.0451 mmol) was added to the solution and allowed to react overnight. The conjugate was purified by precipitation in 1.0 M ammonium sulfate solution followed by centrifugation at room temperature. The pellet containing conjugate and unreacted PNIPAM homopolymer was then resuspended in 20 mM Tris buffer (pH 8) and precipitated a second time. The excess PNIPAM was removed from the second pellet using Ni-NTA affinity chromatography to yield purified conjugate. After collecting the flowthrough, the column was washed with approximately 7 column volumes of wash buffer before elution to completely remove unconjugated PNIPAM. The purified conjugate was dialyzed into pure water. Purity was analyzed using SDS-PAGE and the yield was determined spectrophotometrically.

Sample Preparation and Characterization.

Conjugate solution was concentrated to approximately 44 mg/mL conjugate using Millipore Ultra-15 centrifugal filters with a molecular weight cutoff of 3 kDa. Bulk samples were prepared by evaporation of water either at 40° C. under ambient pressure or at room temperature under vacuum. Solvent annealing was performed at 4° C. or room temperature in sealed jars using nanopure water as the solvent. UV-vis spectra were collected at ambient temperature on a Cary 50 UV-vis spectrophotometer using a quartz cuvette and normalized to the absorbance at 280 nm. CD spectra were obtained using an Aviv Model 202 circular dichroism spectrometer operating at 25° C. and converted into molar ellipticity by correcting for the water background and using the concentration determined by the A$_{280}$. CDPro was used to analyze spectra to determine the secondary structure content using CONTINLL, SELCON3 and CDSSTR methods. Disk-shaped samples for x-ray scattering were cast on kapton tape using 7 mm diameter washers as a mold. SAXS and WAXS data were collected using a Molecular Metrology ASSY 610-004378 system, and corrected for empty cell and dark field scattering. Bulk samples were cryo-microtomed using a Leica EM UC6 at −100° C. to a thickness of 50-60 nm for TEM analysis. Samples were stained with ruthenium tetroxide vapors from a 0.5% aqueous solution for 20-40 minutes. Due to the greater number of alcohol, amine and aromatic functional groups on the protein compared with the polymer, the protein domains were selectively stained and appear dark in images. A JEOL 2000FX Transmission Electron Microscope was used to obtain bright field images using an accelerating voltage of 120 kV and a $LaB_6$ filament. Images were captured using an ORCA camera in a fixed bottom mount configuration.

Volume Fraction Calculation.

The volume fraction of PNIPAM in the mCherry-PNIPAM block copolymer was calculated using mCherry crystallographic data along with a PNIPAM density of 1.05 g/cm³. First, the mCherry density is calculated.

$$\rho = \frac{MW \cdot z}{V \cdot N_A}$$

The molar mass, MW, is 28,134.48 g/mol including the 6× His tag. Z, the number of formula units per unit cell, is 3. $N_A$ is Avogadro's number, and the volume, V, is calculated using the dimensions of the unit cell.

$$V = a \cdot b \cdot c \cdot \sin(\beta)$$

where a=4.876 nm, b=4.285 nm, c=6.106 nm, and β=112.31°.

The volume fraction of PNIPAM is then calculated using the following formula:

$$\varphi_{PNIPAM} = \frac{\frac{MW_{PNIPAM}}{\rho_{PNIPAM}}}{\frac{MW_{PNIPAM}}{\rho_{PNIPAM}} + \frac{MW_{mCherry}}{\rho_{mCherry}}}$$

Termination of Protein Secondary Structure.

Analysis of CD data to quantitatively determine protein secondary structure is provided in Table 2.

Example 2

Fusion Proteins

Example 1 shows that conjugates of globular protein and thermoresponsive polymer can self assemble into lamellar nanostructures with high protein density and preservation of folding. In this Example, carbonic anhydrase (hCAII), an enzyme that converts carbon dioxide and water into bicarbonate and protons, was chosen as a model catalytic globular protein due to its potential application in emission reduction and environmental remediation. A thermoresponsive elastin-like protein (ELP) (as an example of EMPs) was fused to hCAII as a tool for low-cost purification and to direct self-assembly of the enzyme into nanostructured plastics and hydrogels.

Figure 12:
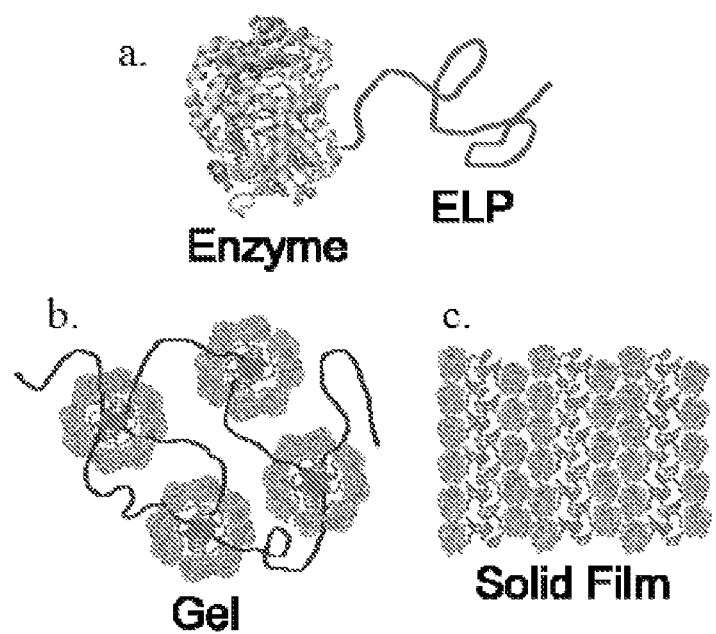
FIG. 12 illustrates that the elastin-like protein (ELP) attached to the enzyme serves to both purify and immobilize the enzyme on high-density gels or solid state films while maintaining low cost requirements.

Currently, affinity interactions are widely used for simple, efficient protein purification. Due to the high costs of these methods, several authors have developed techniques using an elastin-like protein (ELP) as a genetically encoded tag. Thermal or salt precipitation is used to purify the enzyme-ELP fusion protein, and the ELP is subsequently cleaved. Rather than cleaving the ELP, the ELP was used here to direct self-assembly into protein-containing nanodomains, as shown in FIGS. 12b and 12c. FIG. 12a shows how these ELP fusion proteins resemble typical block copolymers, where one block is an enzyme, and the other is a random coil protein. By modifying methods disclosed in Example 1, the ELP was used and led to self-assembly of high-density enzyme arrays containing at least fifty percent enzyme by dry weight.

1. Cloning of Carbonic Anhydrase-ELP Fusion Protein.

The human carbonic anhydrase gene modified so there was no cysteines in the protein and an ELP gene with LCST over 40° C. was ordered. The DNA was transformed into XL1Blue cells and grown as overnight cultures. The genes were then digested with BamHI and HindIII and run on an agarose DNA gel. The bands at 800 base pairs were cut out and the DNA was extracted from the gel. Finally, the digested genes were ligated with the pQE9 vector and transformed into XL1Blue cells. To create the fusion protein, the carbonic anhydrase in pQE9 was first digested with Spe1, a site at the end of the sequence. The ELP in pQE9 was digested with Nhe1-HF and

TABLE 2

Quantitative analysis of circular dichroism spectra using CD Pro software.

| Sample | Method | Fraction helix | Fraction sheet | Fraction turn | Fraction unordered | Average fraction helix | Average fraction sheet | Average fraction turn | Average fraction unordered |
|---|---|---|---|---|---|---|---|---|---|
| mCherryS131C | CONTINLL | 0.057 | 0.503 | 0.183 | 0.257 | 0.041 | 0.497 | 0.192 | 0.270 |
|  | SELCON3 | 0.071 | 0.501 | 0.142 | 0.286 |  |  |  |  |
|  | CSDDTR | −0.004 | 0.486 | 0.251 | 0.267 |  |  |  |  |
| mCherryS131C-PNIPAM | CONTINLL | 0.027 | 0.393 | 0.202 | 0.378 | −0.003 | 0.433 | 0.219 | 0.351 |
|  | SELCON3 |  |  |  |  |  |  |  |  |
|  | CSDDTR | −0.033 | 0.473 | 0.235 | 0.325 |  |  |  |  |
| Room temperature cast | CONTINLL | 0.021 | 0.394 | 0.198 | 0.386 | −0.067 | 0.462 | 0.224 | 0.381 |
|  | SELCON3 | 0.026 | 0.436 | 0.204 | 0.334 |  |  |  |  |
|  | CSDDTR | −0.248 | 0.557 | 0.271 | 0.421 |  |  |  |  |
| 40 C. cast | CONTINLL | 0.029 | 0.390 | 0.203 | 0.377 | 0.001 | 0.428 | 0.215 | 0.356 |
|  | SELCON3 | −0.006 | 0.427 | 0.213 | 0.366 |  |  |  |  |
|  | CSDDTR | −0.019 | 0.467 | 0.228 | 0.324 |  |  |  |  |
| 4 C. anneal | CONTINLL | 0.020 | 0.381 | 0.196 | 0.404 | −0.016 | 0.413 | 0.206 | 0.396 |
|  | SELCON3 | −0.036 | 0.403 | 0.179 | 0.454 |  |  |  |  |
|  | CSDDTR | −0.032 | 0.456 | 0.244 | 0.332 |  |  |  |  |
| Room temperature anneal | CONTINLL | 0.033 | 0.508 | 0.192 | 0.267 | 0.029 | 0.480 | 0.215 | 0.276 |
|  | SELCON3 | 0.037 | 0.480 | 0.217 | 0.266 |  |  |  |  |
|  | CSDDTR | 0.018 | 0.452 | 0.235 | 0.295 |  |  |  |  |

SpeI, which cut it out of the pQE9 vector. These two fragments were run on a gel and extracted. Finally, they were ligated together and retransformed into XL1Blue cells. From sequencing, it was clear that the fusion protein was formed, as anticipated.

2. Biosynthetic Production of Protein.

The DNA for the fusion protein was transformed into SG13009 cells. A single colony was picked off the plate and allowed to grow in 5 mL of Lysogeny Broth (LB) overnight at 37° C. and shaking at 250 RPM. Each overnight culture was added to a liter of 2XYT and grown at 33° C. until reaching an optical density between 0.8 and 1.2. At this point, it was induced to produce the fusion protein and allowed to continue growing for an additional eight hours. The cells were then separated by centrifugation and frozen overnight. They were then defrosted and lysed with lysozyme and sonication. The proteins were purified using a Ni-NTA resin to isolate the His-tagged proteins using native purification buffers with imidazole, sodium phosphate, sodiumchloride, and beta-mercaptoethanol; this mixture was then dialyzed into water.

3. Activity Assays.

To measure the activity of the fusion protein, an esterase assay was used. The assay measured the conversion of 4-nitrophenyl acetate to 4-nitrophenol, a side reaction carbonic anhydrase catalyzes. A buffer of Tris-$SO_4$ at pH 7.6 was used to dilute the fusion protein to 100-200 units/mL. A solution of 3 mM 4-nitrophenyl acetate was prepared. Finally, the buffer and the 4-nitrophenyl acetate mixture were added together in a 2:1 ratio in a crystal cuvette. This was considered the blank and was held at 0° C. for 5 minutes in a UV-Vis spectrophotometer, which measured the absorbance at 348 nm every 0.1 seconds for 5 minutes. The same procedure was run with the diluted protein. Overall, the reaction mixture was 1 mL, with 10 mM Tris-$SO_4$, 1 mM 4-nitrophenyl acetate, and 3-4 units carbonic anhydrase. To calculate the activity, the maximum slope of the blank was subtracted from the maximum slope of the test (in $A_{348}$/s), multiplied by 1000 (to convert to millimoles), and divided by 5.0 (the extinction coefficient of 4-nitrophenol).

4. Pellet Activity Assays.

To test the activity of the fusion protein before purification, a 1 mL sample of broth was centrifuged at 21.1×g for a minute to isolate cells. Next, 50 times the OD at 600 nm of lysis buffer was added to the cells and vortexed until the cells were resuspended and were then sonicated with a bath sonicator. Finally, the lysate was clarified by centrifuging for approximately 5 minutes and using the supernatant in the activity assay, described above.

5. Small Angle X-Ray Scattering.

The dialyzed protein was concentrated using centrifugation filters to approximately 50 mg/mL. To cast the samples into thin films, the concentrated solution was dried at room temperature under vacuum in 50 μL aliquots. Small Angle X-Ray Scattering was performed at Brookhaven National Lab (beamline X9) to determine whether the structure had self-assembled.

Figure 13:
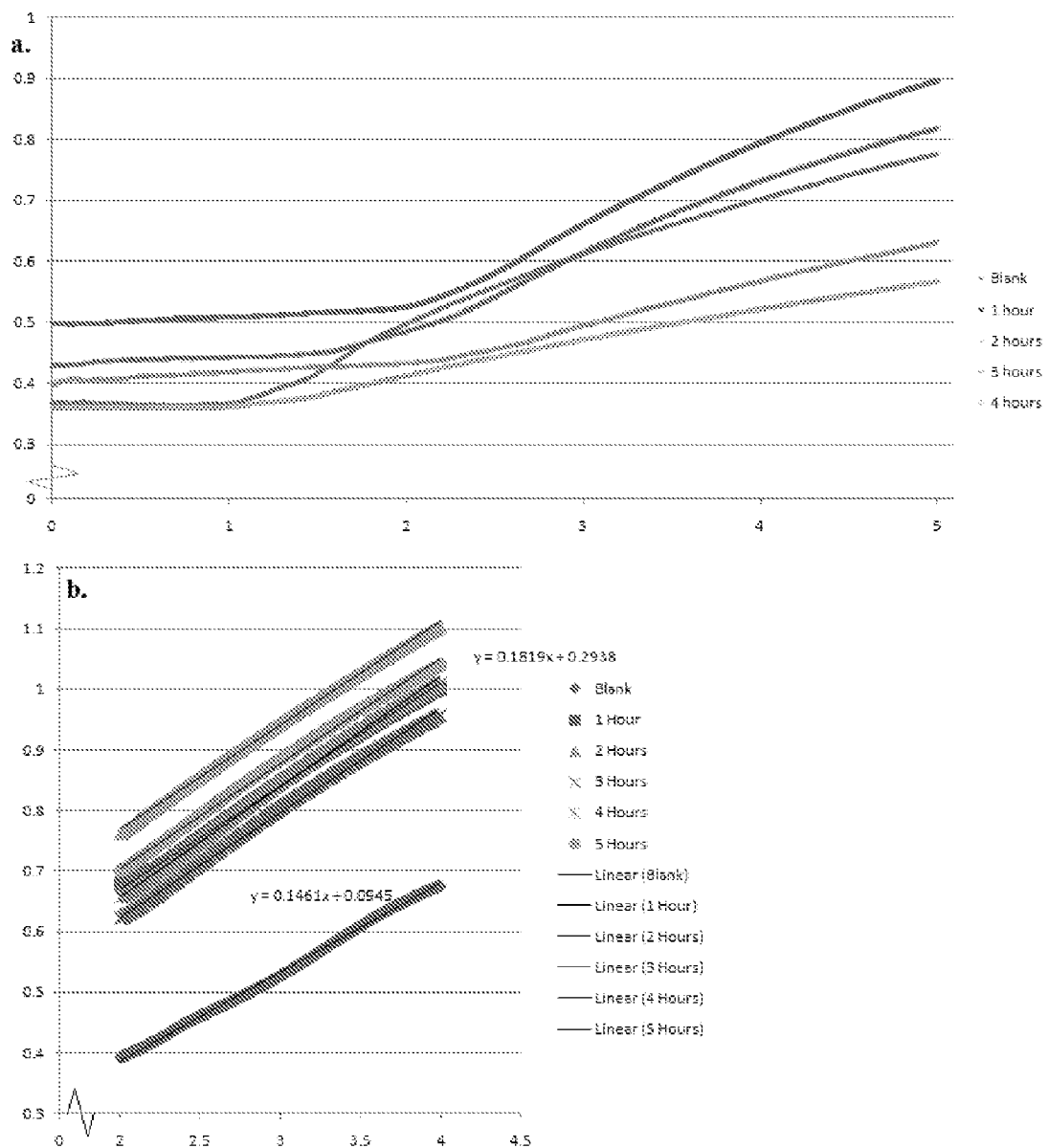
FIG. 13 shows typical results of the activities of test expressions of hCAII at 37° C. (a) and 33° C. (b). It is clear that activity is minimal in the sample produced at 37° C., given that the blank has such a high slope. However, at 33° C. there is a considerably higher slope with the sample than with the blank.
Figure 14:
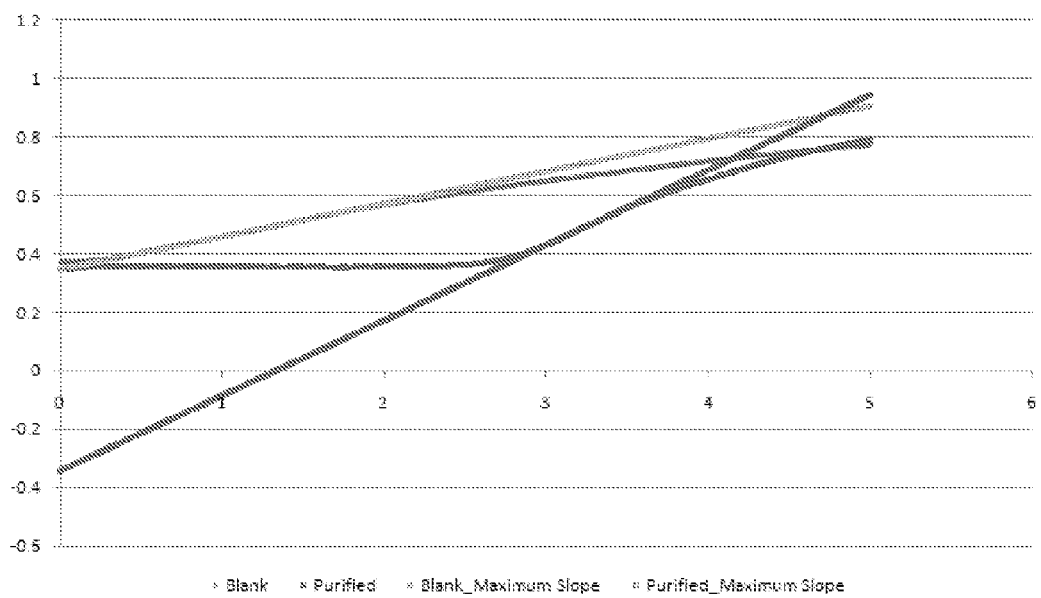
FIG. 14 shows typical results of purified carbonic anhydrase assay. It is clear that the effect of the enzyme is large, as the slope (rate of reaction) increases dramatically with the enzyme in solution.

Data suggests that the fusion protein is self-assembling. High activity of the enzyme, carbonic anhydrase (hCAII), implies that it is correctly folded, which may facilitate self-assembling. In addition, without high activity, there is little industrial use for an enzymatic film. To maximize activity, various temperatures and media were tested. As shown in FIG. 13, the activity (comparing the maximum slope of the blank to the maximum slope of the sample with enzyme in it) is considerably higher at 33° C. than at 37° C. It was also found that in terms of broth, 2XYT had much more activity than TB. From this, it was determined that future expressions of both hCAII and the fusion protein would be at 33° C. and in 2XYT. Unfortunately, these assays do not give meaningful quantitative results. FIG. 14 shows a sample of purified carbonic anhydrase made at 37° C. The maximum slope found of the sample was 0.2575 and the maximum slope of the blank was 0.1119. Using the formula discussed, the activity was 0.485, which is approximately 77% of the literature value.

Figure 15:
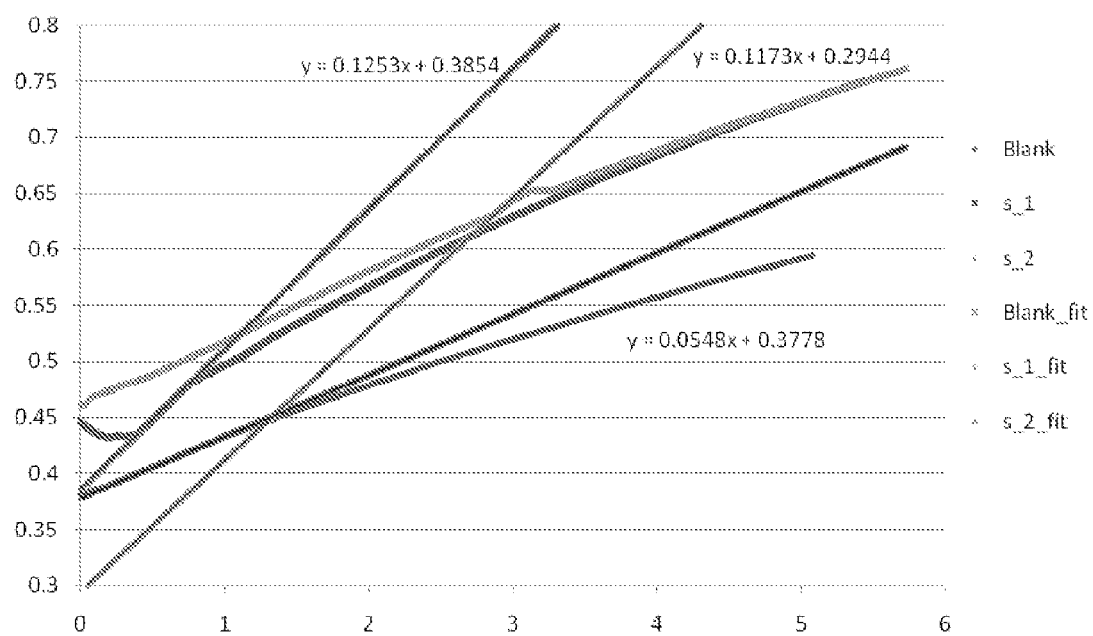
FIG. 15 shows typical results of enzymatic activity assay for a fusion protein as described in Example 2. Date suggests that the protein is active as the rate is much higher when carbonic anhydrase is in the solution.

To make a thin film, the fusion protein was made and its activity was checked. As is visible in FIG. 15, it is clear that the carbonic anhydrase portion of the fusion protein is still active. The film was then cast and run on SAXS. The presence of a strong peak indicates that the fusion protein self-assembled. The location of the primary peak indicates a domain spacing of 20.3 nm.

Figure 16:
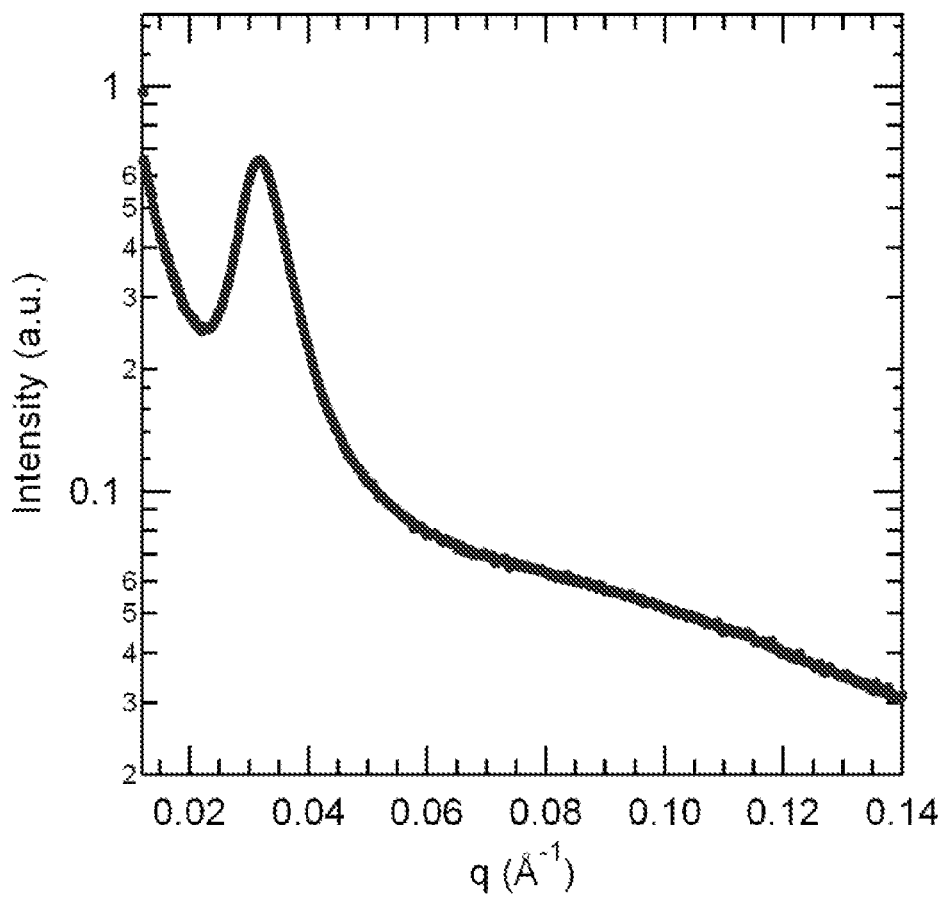
FIG. 16 shows typical small angle x-ray scattering data showing the self-assembly of the fusion protein, carbonic anhydrase-ELP.

As shown in FIG. 16, small angle x-ray scattering was used to show that the carbonic anhydrase-ELP fusion protein for self-assembled nanostructures. A sharp primary peak is present which indicates microphase separation between carbonic anhydrase rich and ELP rich domains.

Example 3

Processing with Additives

Figure 17:
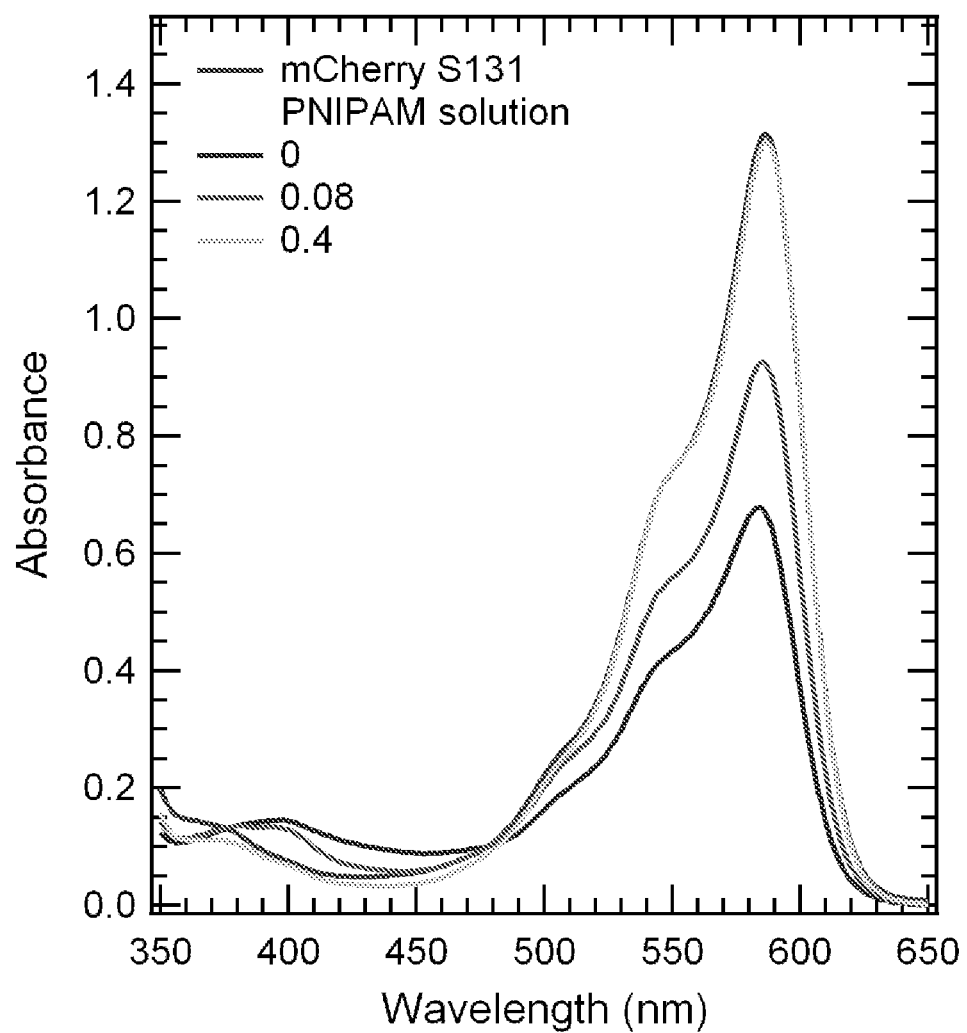
FIG. 17 illustrates typical UV-vis spectra showing the fluorescence of mCherry protein in a mCherry-PNIPAM conjugate as a function of added glycerol. Each spectrum corresponds to a unique weight percent loading of glycerol.

Small molecules have been added to protein-polymer block copolymer materials in order to improve the activity and stability of the protein component. Two additives were tested, trehalose and glycerol. FIG. 17 shows a UV-vis activity assay of our mCherry-PNIPAM material with varying amounts of glycerol added. From this data, at 40% by weight added glycerol, the same protein activity as measured in solution before self-assembly was achieved.

Figure 18:
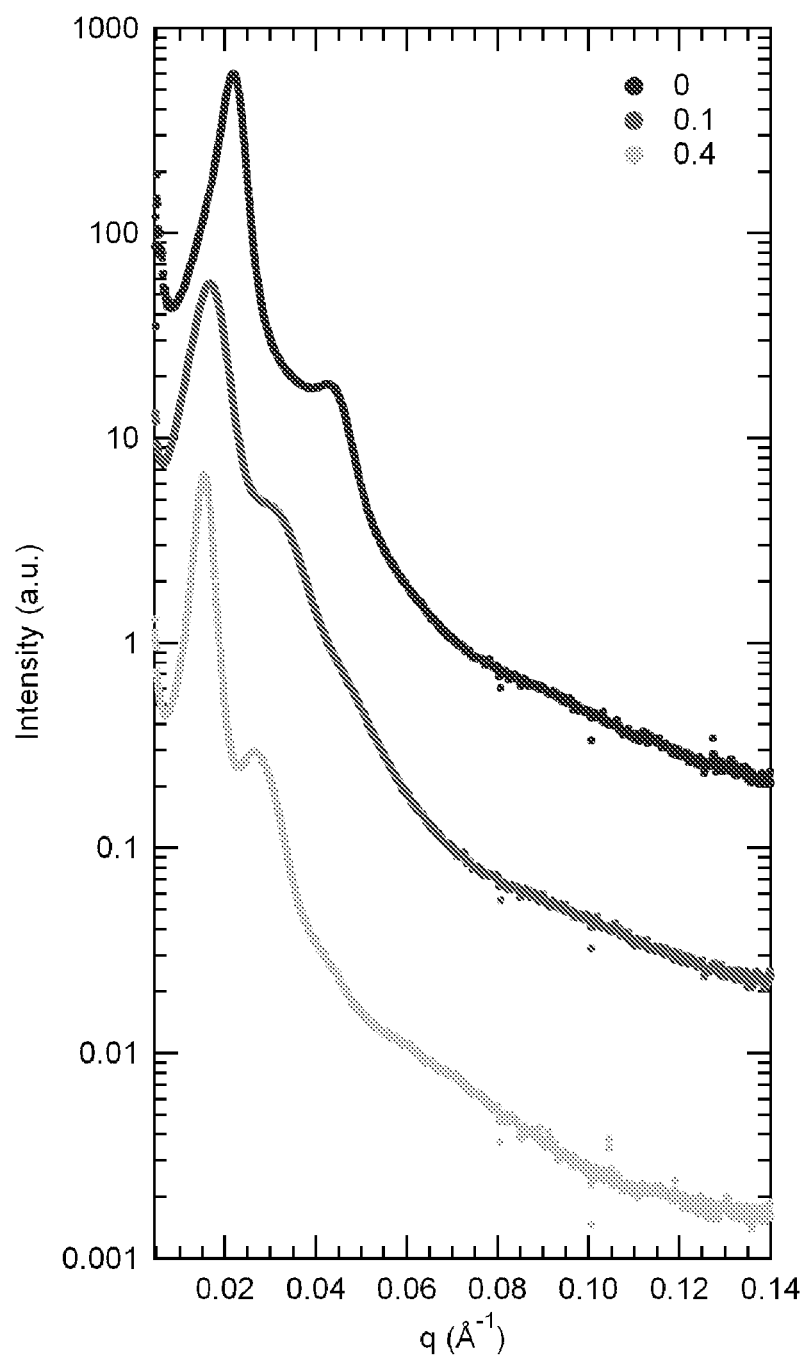
FIG. 18 shows typical small angle x-ray scattering data showing that self-assembled morphology is not significantly altered by the addition of glycerol. Each curve corresponds to at weight percent loading of glycerol.

Small angle x-ray scattering was used to study the materials (FIG. 18) and to ensure that the additive does not disrupt the self-assembly behavior. In these SAXS curves we see peaks indicative of block copolymer ordering. Even with up to 40% by weight glycerol, ordering is still observed. By using small molecule additives such as glycerol, it is shown that the active fraction of protein in the material can be increased, while still have the ability to self-assemble into nanostructured domains.

The processing pathway dependence of protein activity, stability and self-assembled morphology was also investigated. Four types of solvents was employed in this study: protein selective, polymer selective, non-selective, and a non-solvent. The protein selective solvent was an aqueous solution at pH=7.5 and 40° C. which is above the lower critical solution temperature (LCST) of the PNIPAM. The polymer selective solvent was an aqueous solution at pH=5.7 and room temperature. This pH is near the isoelectric point of the protein, and has been used by others to create an environment in which proteins can precipitate out of solution. The non-selective solvent is water at pH=7.5 and room temperature. This is a good solvent for both blocks of our copolymer. The non-solvent is an aqueous solution at pH=5.7 and 40 C which is not a good solvent for either block.

In these studies the highest fraction of functional materials was maintained by casting from a non-selective solvent followed by solvent annealing with a non-selective solvent. This was determined by measuring the material absorbance at 586 nm, as was done with previous activity assays. The thermal stability of these materials were also investigated, and it is found that the samples which were cast from and subsequently solvent annealed in a non-selective solvent were generally thermally stable to 50° C.

OTHER EMBODIMENTS AND EQUIVALENTS

Although this disclosure has described and illustrated by reference to certain embodiments and examples, it is to be understood that the disclosure is not restricted to those particular embodiments or examples. Rather, the disclosure includes all embodiments that are functional and/or equivalents of the specific embodiments and examples that have been described.

We claim:

1. An assembled solid-state or gel-state nanostructure comprising: a plurality of conjugates, wherein each comprises a globular protein conjugated with a polymer that preserves the folded and functional structure of a protein and wherein the weight percentage of the globular protein in the assembled nanostructure is greater than 20%.

2. The assembled nanostructure of claim 1, further comprising an additive.

3. An assembled solid-state or gel-state nanostructure comprising: a plurality of fusion proteins, wherein each comprises a globular protein conjugated with an elastin-mimic polymer (EMP) and wherein the weight percentage of the globular protein in the assembled nanostructure is greater than 20%.

4. A method of forming an assembled nanostructure, comprising:
   providing a plurality of conjugates in an aqueous solution, wherein each of the conjugates comprises a globular protein conjugated with a polymer that preserves the folded and functional structure of the protein;
   removing the aqueous solution so that the conjugates self-assemble to form a solid-state or gel-state nanostructure, wherein the weight percentage of the globular protein in the assembled nanostructure is greater than 20%.

5. The method of claim 4, further comprising a step of adding an additive to the aqueous solution before removing the aqueous solution.

6. The assembled nanostructure of claim 1, wherein the assembled nanostructure has a lamellar structure, a perforated lamellar structure, and/or a hexagonally packed structure.

7. The assembled nanostructure of claim 1, wherein the globular protein is an enzyme.

8. The assembled nanostructure of claim 1, wherein the polymer is a synthetic polymer.

9. The assembled nanostructure of claim 1, wherein the globular protein is covalently conjugated to the polymer.

10. The assembled nanostructure of claim 1, wherein the polymer has a transition temperature greater than 0° C.

11. The assembled nanostructure of claim 6, wherein the polymer has a transition temperature less than 80° C.

12. The assembled nanostructure of claim 1, wherein the polymer has a transition temperature in a range of 25° C. to 70° C.

13. The assembled nanostructure of claim 1, wherein the polymer has a molecular weight greater than 5 kDa.

14. The assembled nanostructure of claim 1, wherein the polymer has a molecular weight in a range of 5 kDa to 100 kDa.

15. The assembled nanostructure of claim 8, wherein the polymer is selected from the group consisting of poly(N-isopropylacrylamide), poly(3-[N-(2-methacroyloyethyl)-N,N-dimethylammonio]propane-sulfonate), poly(hydroxypropyl acrylate), poly(ethylene glycol methyl ether acrylate-b-methoxyethoxy ethyl acrylate) and any combination thereof.

16. The assembled nanostructure of claim 1, wherein the globular protein is a fluorescent protein.

17. The assembled nanostructure of claim 1, wherein the molecular weight of the globular protein is greater than 10 kDa.

18. The assembled nanostructure of claim 3, wherein the EMP comprises the repeat unit of Val Pro Gly Xaa Gly (SEQ ID No:1), wherein Xaa is selected from the group consisting of Val, Leu, Ile, Ala and Gly.

* * * * *